(12) United States Patent
Klokov et al.

(10) Patent No.: US 11,738,054 B2
(45) Date of Patent: Aug. 29, 2023

(54) METHOD TO IMPROVE THERAPEUTIC PROPERTIES OF STEM CELLS

(71) Applicant: ATOMIC ENERGY OF CANADA LIMITED/ÉNERGIE ATOMIQUE DU CANADA LIMTÈE, Chalk River (CA)

(72) Inventors: Dmitry Klokov, Chalk River (CA); Soji Sebastian, Petawawa (CA); Yevgeniya Le, Deep River (CA)

(73) Assignee: ATOMIC ENERGY OF CANADA LIMITED/ENERGIE ATOMIQUE DU CANADA LIMITÈE, Chalk River (CA)

( * ) Notice: Subject to any disclaimer, the term of this patent is extended or adjusted under 35 U.S.C. 154(b) by 574 days.

(21) Appl. No.: 16/631,233

(22) PCT Filed: Jul. 20, 2018

(86) PCT No.: PCT/CA2018/050883
§ 371 (c)(1),
(2) Date: Jan. 15, 2020

(87) PCT Pub. No.: WO2019/014774
PCT Pub. Date: Jan. 24, 2019

(65) Prior Publication Data
US 2020/0230180 A1 Jul. 23, 2020

Related U.S. Application Data

(60) Provisional application No. 62/534,905, filed on Jul. 20, 2017.

(51) Int. Cl.
| | | |
|---|---|---|
| *A61K 35/545* | (2015.01) | |
| *A61K 35/34* | (2015.01) | |
| *A61K 35/44* | (2015.01) | |
| *A61K 41/00* | (2020.01) | |
| *A61P 21/00* | (2006.01) | |

(52) U.S. Cl.
CPC ............ *A61K 35/545* (2013.01); *A61K 35/34* (2013.01); *A61K 35/44* (2013.01); *A61K 41/0057* (2013.01); *A61P 21/00* (2018.01)

(58) Field of Classification Search
CPC .................................................. A61K 35/545
See application file for complete search history.

(56) References Cited

FOREIGN PATENT DOCUMENTS

WO 2016102735 A1 6/2016

OTHER PUBLICATIONS

Young, Am J Transl Res . 2017, vol. 9, 1914-1921, Abstract; Figures1 and 2; p. 1920.*
Yang, et al. Low-dose radiation modulates human mesenchymal stem cell proliferation through regulating CDK and Rb. Am J TranslRes. Apr. 30, 2017 (Apr. 30, 2017), vol. 9, pp. 1914-1921.*
Liang, The low-dose ionizing radiation stimulates cell proliferation via activation of the MAPK/ERK pathway in rat cultured mesenchymal stem cells. J Radiat Res. Mar. 24, 2011 (Mar. 24, 2011), vol. 52, pp. 380-386.*
Li, Stem Cells International, vol. 2016, Article ID 9682757, 14 pages.*
Eong, Scientific Reports, 7, 13718, 2017.*
Translation of Office Action in JP Application No. 2020-502587.
Alessio, N. et al., "Low dose radiation induced senescence of human mesenchymal stromal cells and impaired the autophagy process", Oncotarget, 6, 2015, 8155-8166.
Azzam, E. I. et al., "Radiation-Induced Adaptive Response for Protection against Micronucleus Formation and Neoplastic Transformation in C3H 1 0T1 /2 Mouse Embryo Cells", Radiation Research, 138, 1994, S28-S31.
Bahari-Kashami, J. et al., "Low dose radiation effects in myogenic progenitors: is a little bit of radiation good for themuscle satellite cells?", Am. J. Clin Onco, 34(2), Abstract 47, Apr. 2011, 215.
Baldwin, J. et al., "Radiation Hormesis: Historical and Current Perspectives", J Nucl Med Technol., 43, 2015, 242-246.
Bengal, E. et al., "Rejuvenating stem cells to restore muscle regeneration in aging", Version 1. F1000Res.; vol. 6, doi: 10.12688/f1000research.9846.1, 2017, 76.
Calabrese, E. J. et al., "Pre-and post-conditioning hormesis in elderly mice, rats, and humans: its loss and restoration", Biogerontology, 17, 2016, 681-702.
Calabrese, E. J. et al., "Preconditioning is hormesis part I: Documentation, dose-response features and mechanistic foundations", Pharmacol. Res., 110, doi: 10.1016/j.phrs.2015.12.021, Aug. 2016, 242-264.
Chal, J. et al., "Differentiation of pluripotent stem cells to muscle fiber to model Duchenne muscular dystrophy", Nat Biotech., 33, 2015, 962-969.
Charge, S. et al., "Cellular and Molecular Regulation of Muscle Regeneration", Physiological Reviews, 84, 2004, 209-238.
Chiche, A. et al., "Injury-Induced Senescence Enables In Vivo Reprogramming in Skeletal Muscle", Cell Stem Cell, 20, e404, 2017, 407-414.
Cho, W. et al., "Low-Dose Ionizing [gamma]-Radiation Promotes Proliferation of Human Mesenchymal Stem Cells and Maintains Their Stem Cell Characteristics", Tissue Eng Regen Med, 14(4), DOI 10.1007/sI3770-017-0045-2, Mar. 14, 2017, 421-432.
Crist, C. et al., "Emerging new tools to study and treat muscle pathologies: genetics and molecular mechanisms underlying skeletal muscle development, regeneration, and disease", The Journal of Pathology, 241, 2017, 264-272.

(Continued)

*Primary Examiner* — Nizal S Chandrakumar
(74) *Attorney, Agent, or Firm* — Joseph C. Zucchero; Carolyn S. Elmore; Elmore Patent Law Group, P.C.

(57) ABSTRACT

In one aspect, a method of preconditioning stem cells comprising exposing stem cells to low dose radiation (LDR) is provided. In another aspect, a population of preconditioned stem cells is provided, wherein the population of 5 preconditioned stem cells is obtained by exposing stem cells to LDR. Uses of the preconditioned stem cells are also provided. In other aspects, the stem cells are muscle stem cells.

13 Claims, 12 Drawing Sheets

(56) References Cited

OTHER PUBLICATIONS

Heissig, B. et al., "Low-dose irradiation promotes tissue revascularization through VEGF release from mast cells and MMP-9-mediated progenitor cell mobilization", JEM, 202(6), Sep. 2005, 739-750.
Jolly, D. et al., "A brief review of radiation hormesis", Australas Phys Eng Sci Med, 32, 2009, 180-187.
Kuang, S. et al., "The emerging biology of satellite cells and their therapeutic potential", Trends in Molecular Medicine, 14, 2008, 82-91.
Liang, X. et al., "The low-dose ionizing radiation stimulates cell proliferation via activation of the MAPK/ERK pathway in rat cultured mesenchymal stem cells", J Radiat Res., 52(3), Jan. 1, 2011, 380-386.
Liu, S. et al., "Strategies to Optimize Adult Stem Cell Therapy for Tissue Regeneration", Int. J. Mol. Sci., 17( 982), Jun. 21, 2016, 1-16.
Maffioletti, S. M. et al., "Efficient derivation and inducible differentiation of expandable skeletal myogenic cells from human ES and patient-specific iPS cells", Nat. Protocols, 10, 2015, 941-958.
Manda, K. et al., "Low dose effects of ionizing radiation on normal tissue stem cells", Mutation Research/Reviews in Mutation Research, 761, 2014, 6-14.
Masuda, S et al., "Time- and dose-dependent effects of total-body ionizing radiation on muscle stem cells", Physiol Rep., 3(4), Apr. 1, 2015, e12377.
Mieloch, A. A. et al., "The concept of radiation-enhanced stem cell differentiation", Radiol Oncol., 49(3), 2015, 209-216.
Miousse, I. R. et al., "Effects of ionizing radiation on DNA methylation: from experimental biology to clinical applications", Int J Radiat Biol, 93, 2017, 457-469.
Mitchel, R. E. et al., "Low doses of radiation increase the latency of spontaneous lymphomas and spinal osteosarcomas in cancer-prone, radiation-sensitive Trp53 heterozygous mice", Radiat Res, 159, 2003, 320-327.
Mitchel, R. E. et al., "The adaptive response modifies latency for radiation-induced myeloid leukemia in CBA/H mice", Radiation Research, 152, 1999, 273-279.
Nenoi, M. et al., "In vivo radioadaptive response: A review of studies relevant to radiation-induced cancer risk", Hum Exp Toxicol., 34(3), DOI: 10.1177/0960327114537537, Mar. 2015, 272-283.
Ng, R. K. et al., "Epigenetic memory of an active gene state depends on histone H3.3 incorporation into chromatin in the absence of transcription", Nat Cell Biol, 10, 2008, 102-109.
Osipov, A. N. et al., "In vivo γ-irradiation low dose threshold for suppression of DNA double strand breaks below the spontaneous level in mouse blood and spleen cells", Mutation Research/Genetic Toxicology and Environmental Mutagenesis, 756, 2013, 141-145.
Preciado, S. et al., "Mesenchymal Stromal Cell Irradiation Interferes with the Adipogenic/Osteogenic Differentiation Balance and Improves Their Hematopoietic-Supporting Ability", Biol Blood Marrow Transplant, 24(3), Nov. 2017, 443-451.
Sambasivan, R. et al., "Skeletal muscle stem cell birth and properties", Seminars in Cell & Developmental Biology, 18, 2007, 870-882.
Sousa-Victor, et al., "Regenerative decline of stem cells in sarcopenia", Molecular Aspects of Medicine, 50, 2016, 109-117.
Tedesco, F. S. et al., "Repairing skeletal muscle: regenerative potential of skeletal muscle stem cells", J. Clin. Invest., 120, 2010, 11-19.
Vahidi Ferdousi, L. et al., "More efficient repair of DNA double-strand breaks in skeletal muscle stem cells compared to their committed progeny", Stem Cell Res., 13(3 Pt A), DOI:10.1016/j.scr.2014.08.005S1873-5061(14)00094-4, Nov. 2014, 492-507.
Wu, B. et al., "Biological effects of low dose X-irradiation on human bone marrow mesenchymal stem cells", Zhongguo Shi Yan Xue Ye Xue Za Zhi, 19(5), Oct. 1, 2011, 1214-7.
Yaffe, D. et al., "Serial passaging and differentiation of myogenic cells isolated from dystrophic mouse muscle", Nature, 270, 1977, 725-727.
Yang, L. et al., "Low dose radiation modulates human mesenchymal stem cell proliferation through regulating CDK and Rb", Am J Transl Res., 9(4), Apr. 1, 2017, 1914-1921.
Zhou, X-Z., "Low-dose X-irradiation on bone marrow derived mesenchymal stem cells: An in vitro study", Bone, 47 (Abstract 344), Oct. 15, 2010, S442-S443.
Jin, Y-W. et al., "Comprehensive analysis of time—and dose-dependent patterns of gene expression in a human mesenchymal stem cell line exposed to low-dose ionizing radiation", Oncology Reports, 19, Jan. 1, 2008, 135-144.
Koishi, K. et al., "MyoD protein accumulates in satellite cells and is neurally regulated in regenerating myotubes and skeletal muscle fibers", Developmental Dynamics, 202(3), Mar. 1, 1995, 244-254.
Liu, W. et al., "Hypoxia promotes satellite cell self-renewal and enhances the efficiency of myoblast transplantation", Development, 139(16), doi:10.1242/dev.079665, Aug. 15, 2012, 2857-2865.

\* cited by examiner

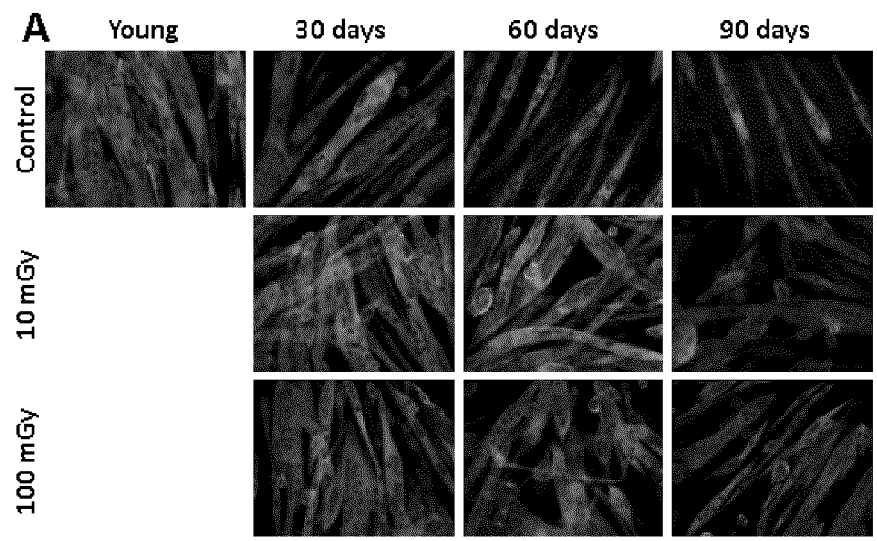
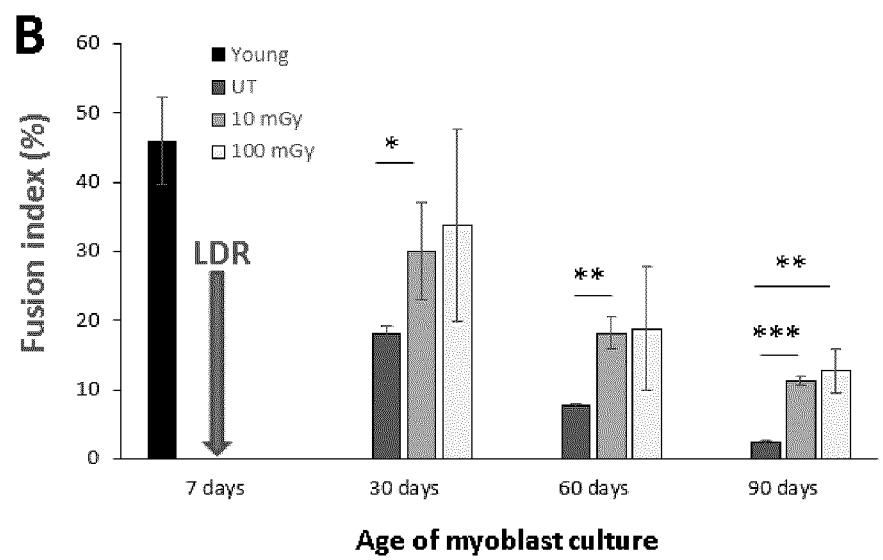
Fig. 3

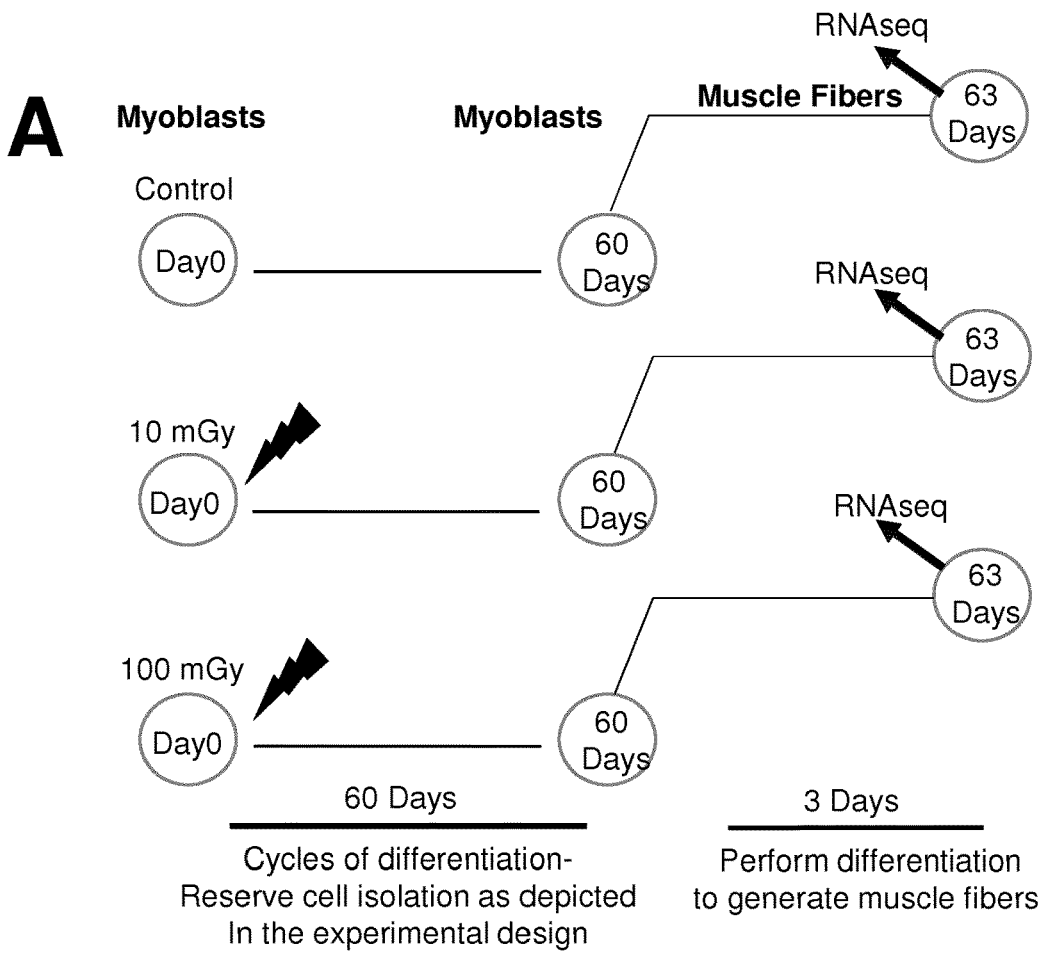
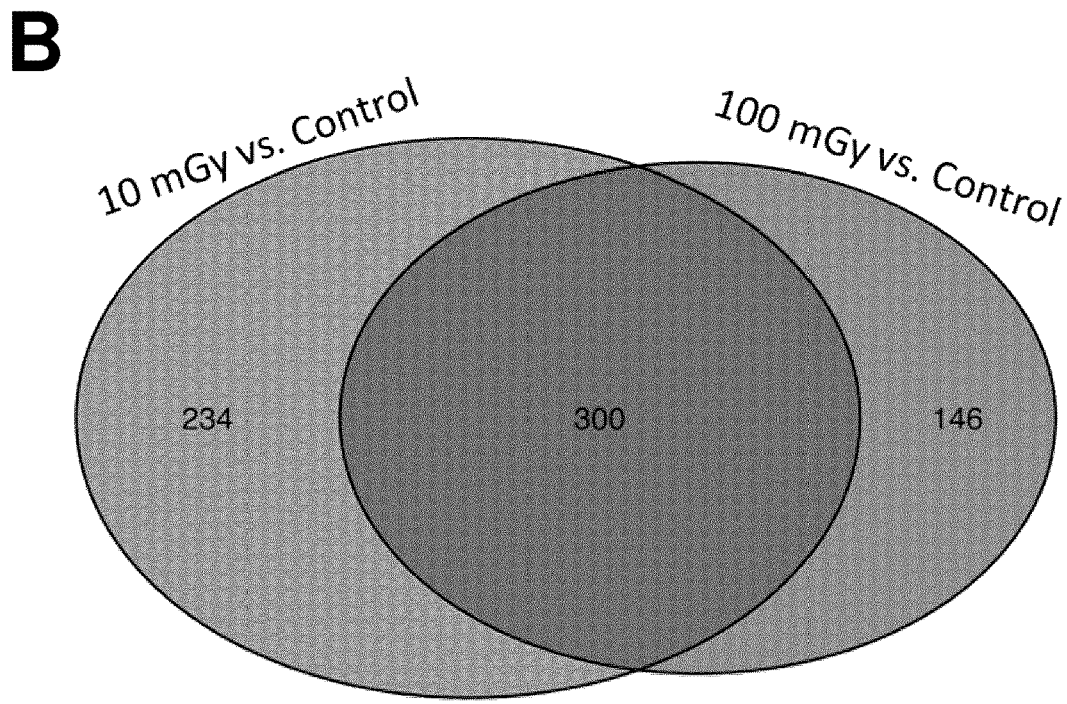
Fig.5  Venn diagram showing the number of differentially upregulated genes in the 10 and 100 mGy normalized to untreated control

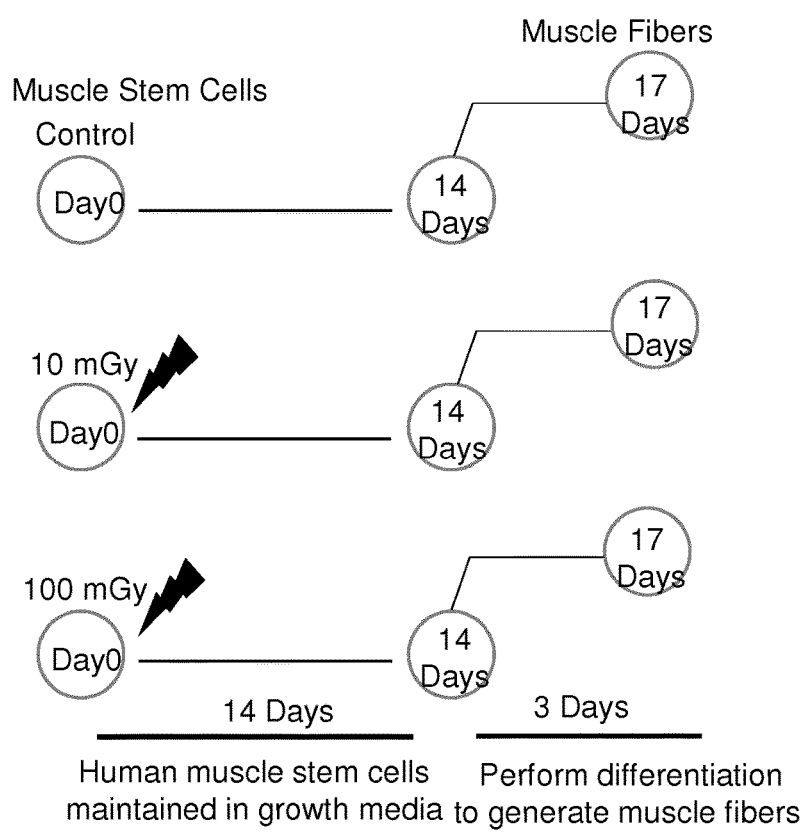
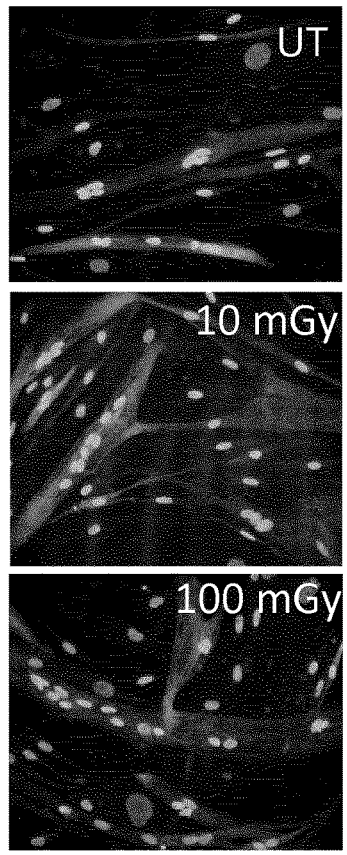
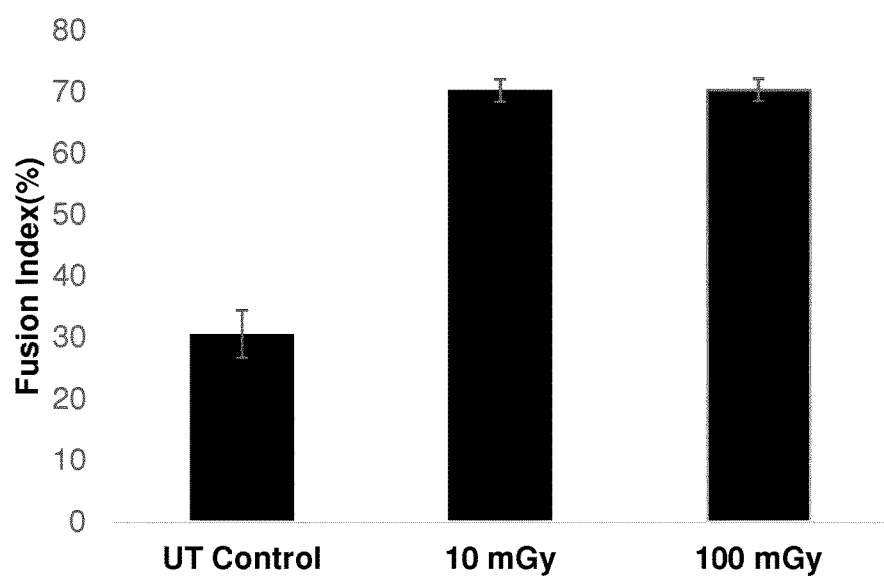
Fig.7

METHOD TO IMPROVE THERAPEUTIC PROPERTIES OF STEM CELLS

CROSS-REFERENCE TO RELATED APPLICATION

This application claims the benefit U.S. Provisional Application No. 62/534,905 filed Jul. 20, 2017 and entitled Method to Improve Therapeutic Properties of Stem Cells, the entirety of which is incorporated herein by reference.

FIELD

The present disclosure relates to methods for improving the regenerative and therapeutic properties of stem cells and stem cells obtained using the disclosed methods. In particular, the disclosure relates to methods for improving the regenerative and therapeutic properties of stem cells by exposing the cells to low dose radiation (LDR). The disclosure also relates to stem cells that have been exposed to LDR, and methods of use thereof.

BACKGROUND

Skeletal muscle is the largest organ in human body and its long-term maintenance depends on muscle stem cells, otherwise known as satellite cells. They represent the major population of resident stem cells in adult skeletal muscle [Sambasivan and Tajbakhsh, 2007]. These adult stem cells facilitate the postnatal growth, remodeling and repair of the muscle tissue. Upon muscle injury, routinely experienced by humans during any physical activity, satellite cells relocate from the surface of muscle fibers to the area of injury across the muscle mass and proliferate extensively [Charge et al., 2004]. During this proliferation they adopt one of two fates: 1) self-renewal and switching back to stand-by mode (can be called reserve cells), or 2) differentiation to form myoblasts that will fuse with damaged muscle fibers to repair the muscle. In fact, the regenerative capacity of skeletal muscle makes it one of the best-studied examples of mammalian tissue regeneration. Consequently, there is great promise for the treatment of muscle diseases using satellite cells [Aziz et al., 2012].

Muscle diseases can be broadly divided into a) genetic (e.g. Duchenne muscle dystrophy, facioscapulohumeral muscular dystrophy), b) aging related (e.g. sarcopenia) and c) other disease related (e.g. cachexia associated with cancer, kidney failure, chronic obstructive pulmonary disease or others). Collectively, the family of muscular dystrophies represents a major medical issue and currently there is no cure for any of them. Intensive efforts have been made towards developing regenerative therapeutic strategies that include the use of satellite cells [Bengal et al., 2017, Crist, 2017].

In the last decade, progress has been made in methods for isolation and moderate enrichment of satellite cells. However, due to a number of limitations these efforts have yet to translate into efficient modalities to treat muscle diseases. For example, one of the limitations is related to low yields of satellite cells that are not sufficient for therapeutic transplantation purposes [Kuang and Rudnicki, 2008]. Ex vivo expansion may improve the final yield; however, rounds of passaging typically lead to loss of stemness, accumulation of DNA damage, higher immunogenicity and other undesirable outcomes. Subsequently, these can result in immunological rejection after transplantation and inefficient muscle fiber formation/regeneration. In addition, muscle stem cells are unable to travel great distances from the point of injection, causing poor integration into host muscles. It is not surprising that clinical trials using satellite cells or myoblasts for treating muscle disease have not yet been successful [Tedesco et al., 2010]. Alternative approaches include the use of pluripotent human embryonic stem cells (hES) or induced human pluripotent stem cells (ihPS) [Maffioletti et al., 2015]. Yet, lengthy protocols of directed satellite cell production from hES or ihPS cells may still suffer from issues related to in vitro growth and expansion [Chal et al., 2015]. Therefore, there is a need for preconditioning of in vitro or ex vivo maintained muscle stem cells that would help preserve and/or improve their muscle and stem cell identity and other qualities or functions that are key to successful therapy.

SUMMARY

Although the existence of a multipotent entity that gives rise to all cells in the body or a specific tissue lineage e.g., blood, was postulated in 1909 by a Russian scientist Alexander Maximow, it was not until recently that the concept of an adult tissue stem cell (SC) was recognized and accepted1. We now know that almost all tissues in the body harbour a small subset of multipotent, quiescent cells capable of self-renewal, proliferation and differentiation into mature cellular subtypes. These cells are activated upon tissue damage, mobilize, divide and differentiate to replace diseased, aging or damaged tissues. With the discovery of the unique properties of stem cells and their regenerative capacity came the possibility of utilizing these cells for therapeutic purposes.

While very promising, stem cell therapy is thwarted by the challenge of obtaining SCs in numbers that are sufficient to support therapy development. Stem cells constitute a very small percentage of all adult cells in a given tissue—on the order of 0.01-0.001%. Therefore, it is necessary to expand stem cells in vitro using specialized media formulations. Unfortunately, this ex-vivo manipulation of stem cells leads to their premature aging, loss of stemness and significantly decreased functional and regenerative capacity4. As a result, the only currently approved stem cell therapy in North America is hematopoietic stem cell transplantation, which does not require any ex-vivo stem cell expansion. Thus, methods that delay stem cell aging and improve SCs functional and regenerative capacity following expansion in vitro are highly desirable.

This disclosure describes improving the regenerative and therapeutic properties of stem cells by exposing the cells to low dose radiation (LDR). In some examples, the methods described herein can be used to help retard the aging and age-related degradation of one or more attributes and/or properties of the particular stem cell type. That is, aged irradiated stem cells may experience less age-related degradation of one or more target attributes when compared to young stem cells than an aged, non-irradiated stem cell. For example, stem cells that are irradiated may exhibit slower declines in one or more of their attributes, such as proliferation, differentiation, fusion index as the cells age, than non-irradiated stem cells of the same type.

In one example, the inventors have demonstrated that irradiated muscle stem cells may exhibit less age-related degradation of one or more attributes such as their efficiency to the capacity of myoblasts to differentiate into muscle fibers is enhanced if the cultures are exposed to LDR. The inventors have also demonstrated that the techniques described herein may, in some instances and for some types of stem cells, help enhance a functional capacity of stem cells and/or may help delay at least some aspects of age-associated decline in function. The inventors have also demonstrated that upon stimulated differentiation markers of myogenesis are increased in cultures of myoblasts that have been exposed to LDR compared to unirradiated controls.

In other examples, the inventors have demonstrated that irradiated mesenchymal stem/stromal and progenitor cells (MSC/MSPC) may exhibit less age-related degradation of one or more attributes such as proliferation and/or differentiation, as compared to non-irradiated stem cells of the same type and of analogous age/condition.

In other examples, the inventors have demonstrated that irradiated endothelial colony forming cells (ECFCs)/endothelial stem cells (ESCs) suffer less age-related degradation of one or more attributes such as proliferation and/or migration potential, as compared to non-irradiated stem cells of the same type and of analogous age/condition.

In accordance with one broad aspect of the teachings described herein, a method of preconditioning stem cells may include exposing stem cells to low dose radiation (LDR), which may help provide preconditioned stem cells. This may, for example, enhance the functional capacity of stem cells and may help delay age-associated decline in stem cell function as compared to similar stem cells that are not irradiated.

The radiation may be ionizing radiation, and optionally may be γ-radiation or X-ray radiation.

The cells may be exposed to 1 to 500 mGy of radiation, and optionally 5 to 200 mGy of radiation or 8 to 150 mGy of radiation.

The stem cells may be muscle stem cells.

The stem cells may be mesenchymal stem/stromal and progenitor cells.

The stem cells may be endothelial colony forming cells/endothelial stem and progenitor cells.

The stem cells may be hematopoietic stem and progenitor cells.

The stem cells may be human stem cells or optionally may be mouse stem cells.

The stem may be exposed to LDR in vitro or ex vivo.

The preconditioned muscle stem cells may in some instances show increased differentiation into muscle fibers compared to muscle stem cells that have not been exposed to LDR.

The preconditioned muscle stem cells may in some instances have higher expression of at least one marker selected from the group consisting of myogenin, MyH3, MyoD, TKS5 and TMEM8c compared to muscle stem cells that have not been exposed to LDR.

The method may include the step of administering the preconditioned stem cells to a subject in need thereof.

The subject may be a human.

The subject may have a muscle disease.

A population of preconditioned stem cells may be provided, and may be obtained by exposing stem cells to low dose radiation (LDR).

The radiation may be ionizing radiation, and optionally may include γ-radiation or X-ray radiation.

The cells may be exposed to from about 1 to about 500 mGy of radiation, and optionally from about 5 to about 200 mGy of radiation or from about 8 to about 150 mGy of radiation. The stem cells may be muscle stem cells.

The stem cells may be mesenchymal stem/stromal and progenitor cells.

The stem cells may be endothelial colony forming cells/endothelial stem/progenitor cells.

The stem cells may be human stem cells or optionally may be mouse stem cells.

The preconditioned muscle stem cells may show increased differentiation into muscle fibers compared to muscle stem cells that have not been exposed to LDR.

The preconditioned muscle stem cells may have higher expression of at least one marker selected from the group consisting of myogenin, MyH3, MyoD, TKS5 and TMEM8c compared to muscle stem cells that have not been exposed to LDR.

In accordance with another broad aspect of the teachings described herein, a pharmaceutical composition may include a cell population of preconditioned stem cells, including those described herein, and a carrier.

In accordance with another broad aspect of the teachings described herein, a method of treating a muscle disease in a subject may include administering at least some preconditioned stem cells described herein to a subject in need thereof. The preconditioned stem cells may be muscle stem cells.

The preconditioned muscle stem cells described herein may be used for treating a muscle disease in a subject in need thereof.

In accordance with another broad aspect of the teachings described herein, a method of preconditioning stem cells may include the steps of:
 a) providing a sample comprising a plurality of target stem cells;
 b) irradiating the target stem cells with a first dose of radiation emitted from a radiation source during an irradiation period to convert the target stem cells to irradiated, preconditioned stem cells suitable for use in a subsequent therapeutic treatment process.

Irradiating the target stem cells may reduce age-associated decline of at least a first cellular function of each target stem cell.

The first cellular function may have an initial performance value and may define an aged performance value at a threshold aging time. The preconditioned stem cells may have a treated performance value at the threshold aging time that may be between the aged performance value and the initial performance value, and may be higher in some instances.

The treated performance value may be closer to the initial performance value than the aged performance value.

The target stem cells may each include a second cellular function having a second initial performance value and defining a second aged performance value at a second threshold aging time. The preconditioned stem cells may have a second treated performance value at the second threshold aging time and it may be between the second aged performance value and the second initial performance value.

The second threshold aging time may be different than the first threshold aging time.

The second treated performance value may be closer to the second initial performance value than the second aged performance value.

At least one of the threshold aging time and the second threshold aging time may be determined by the completion of a threshold number of cell passages.

The threshold number of cell passages may be greater than 4, and may be between 4 and 23.

At least one of the threshold aging time and the second threshold aging time may be determined by a time elapsed in a cell culture.

The target stem cells may include muscle stem cells. The first cellular function may include cellular fusion, the initial performance value may include an initial fusion index, the aged performance value may include an aged fusion index, and the treated performance value may include a treated fusion index.

The treated fusion index may be greater than the aged fusion index.

The treated fusion index may be at least twice the aged fusion index.

The treated fusion index may be more than 50%, and may be more than 60% and more than 70%.

The preconditioned stem cells may show increased differentiation into muscle fibers compared to target stem cells that are not irradiated.

The preconditioned stem cells may have higher expression of at least one marker selected from the group consisting of myogenin, MyH3, MyoD, TKS5 and TMEM8c compared to target stem cells that are not irradiated.

The target stem cells may include mesenchymal stem cells. The first cellular function may include proliferation, the initial performance value may include an initial doubling time, the aged performance value may include an aged doubling time, and the treated performance value may include a treated doubling time.

The treated doubling time may be less than the aged doubling time.

The treated doubling time may be less than 50% of the aged doubling time.

The treated doubling time may be less than three times the initial doubling time.

The threshold number of cellular passages may be between 12 and 15.

The threshold number of cellular passages may be 14 or 15, and optionally may be 15.

The target stem cells may include a second cellular function that is chondrogenic differentiation. A second initial performance value may include an initial differentiation capacity, a second aged performance value may include an aged differentiation capacity at a second threshold aging time, and a second treated performance value may include a treated differentiation capacity at the second threshold aging time.

The target stem cells may include mesenchymal stem cells.

The first cellular function may be chondrogenic differentiation, the initial performance value may include an initial differentiation capacity, the aged performance value may include an aged differentiation capacity, and the treated performance value may include a treated differentiation capacity.

The treated differentiation capacity may be greater than the aged differentiation capacity.

The treated differentiation capacity may be greater than the initial differentiation capacity.

The treated differentiation capacity may be at least 60% of the initial differentiation capacity.

The treated differentiation capacity may be at least 150% of the aged differentiation capacity.

A difference between the treated differentiation capacity and the initial differentiation capacity may be less than a difference between the aged differentiation capacity and the initial differentiation capacity.

The target stem cells may include endothelial colony forming cells. The first cellular function may be proliferation, the initial performance value may include an initial doubling time, the aged performance value may include an aged doubling time, and the treated performance value may include a treated doubling time.

The treated doubling time may be less than the aged doubling time.

The treated doubling time may be less than the aged doubling time.

The threshold aging time may be defined by a threshold number of cellular passages that is between 5 and 8, 6 and 8, 7 or 8, and optionally may be at least 5 or at least 8.

A second cellular function may be migration. A second initial performance value may include an initial time to achieve a predetermined confluency, a second aged performance value may include an aged time to achieve the predetermined confluency at the second threshold time, and a second treated performance value may include a treated time to achieve the predetermined confluency at the second threshold time.

The predetermined confluency may be at least 60%.

The treated time to achieve a predetermined confluency may be less than the aged time to achieve the predetermined confluency.

The treated time to achieve the predetermined confluency may be between about 1.4 and 1.8 times the initial time to achieve the predetermined confluency.

The target stem cells may include endothelial colony forming cells. The cellular function may include migration, the initial performance value may include an initial time to achieve a predetermined confluency, the aged performance value may include an aged time to achieve the predetermined confluency, and a treated performance value may include a treated time to achieve the predetermined confluency.

The predetermined confluency may be at least 60%.

The treated time to achieve a predetermined confluency may be less than the aged time to achieve the predetermined confluency.

The treated time to achieve the predetermined confluency may be between about 1.4 and 1.8 times the initial time to achieve the predetermined confluency.

The target stem cells may be human stem cells.

The target stem cells may be mouse stem cells.

The radiation may include ionizing radiation.

The radiation may include low linear energy transfer (LET) ionizing radiation.

The radiation may include at least one of γ-radiation and X-ray radiation, and optionally may be γ-radiation.

The first dose of radiation may include between about 1 and about 500 mGy of radiation.

The first dose of radiation may include between about 2 and about 200 mGy of radiation.

The first dose of radiation comp may include rises between about 2 and about 200 mGy of radiation.

The first dose of radiation may include between about 10 and about 100 mGy of radiation.

The first dose of radiation may be about 10 mGy.

The first dose of radiation is about 50 mGy.

The first dose of radiation may be about 100 mGy.

The target stem cells may be irradiated while in vitro within a subject to be treated.

The target stem cells may be irradiated while ex vivo.

The method may include using the preconditioned stem cells in a subsequent therapeutic process.

The method may include administering the preconditioned stem cells to a subject in need thereof. The subject may be a human, and optionally may have a muscle disease.

In accordance with another broad aspect of the teachings described herein, a population of preconditioned stem cells may be obtained by using the methods described herein The preconditioned stem cells may include muscle stem cells and may show increased differentiation into muscle fibers when compared to target stem cells that have not been exposed to LDR at a threshold aging time.

The preconditioned muscle stem cells may have higher expression of at least one marker selected from the group consisting of myogenin, MyH3, MyoD, TKS5 and TMEM8c compared to muscle stem cells that have not been exposed to LDR.

In accordance with another broad aspect of the teachings described herein, a pharmaceutical composition may include preconditioned stem cells obtained by using the methods described herein in combination with any suitable carrier.

In accordance with another broad aspect of the teachings described herein, a method of treating a muscle disease may include administering preconditioned stem cells is obtained by using the methods described herein to a subject in need thereof.

In accordance with another broad aspect of the teachings described herein, a use of the preconditioned stem cells created in accordance with the methods described herein may be used for treating a muscle disease in a subject in need thereof.

Other features and advantages of the present disclosure will become apparent from the following detailed description. It should be understood, however, that the detailed description and the specific examples, while indicating preferred embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which:

FIG. 3 shows that LDR exposure reverses the decline of myogenic potential with time of culture. A: Immunostaining for muscle specific myosin heavy chain (MHC) by anti-MHC antibody of cultures maintained in differentiation medium for 4 days (magnification 40×). B: Quantification of the fusion index in differentiated C2C12 cultures of various ages with or without LDR. Values are means of three independent experiments.

FIG. 5 shows global gene expression profiling in mouse muscle cells using Next Generation Sequencing. A. Schematic representation of experimental plan for RNAseq by NGS. Young mouse muscle cells acutely irradiated for 10 and 100 mGy doses and aged in culture for 60 days and differentiated to form muscle fibers. Samples were subjected for RNAseq analysis using NGS technique. B. Gene expression in 10 and 100 mGy treated cells were compared to untreated control cells using Cuffdiff NGS analytical tool and differentially expressed genes were represented as a venn diagram.

FIG. 7 shows observed beneficial effects from experiments conducted on biopsy derived human muscle stem cells. A: is a graphical representation of experimental plan, young human muscle stem cells were exposed to LDR (0, 10 or 100 mGy) and maintained in growth media for 14 days and differentiated to form muscle fibers for 3 days in differentiation media containing 2% horse serum. B: Representative immunofluorescence microscopy images from treated and untreated stem cells derived muscle fibers. Graphical representation shows 60-70% increase in fusion index in treated stem cells compared to untreated control stem cells n=3 experiments.

DETAILED DESCRIPTION

Figure 1:
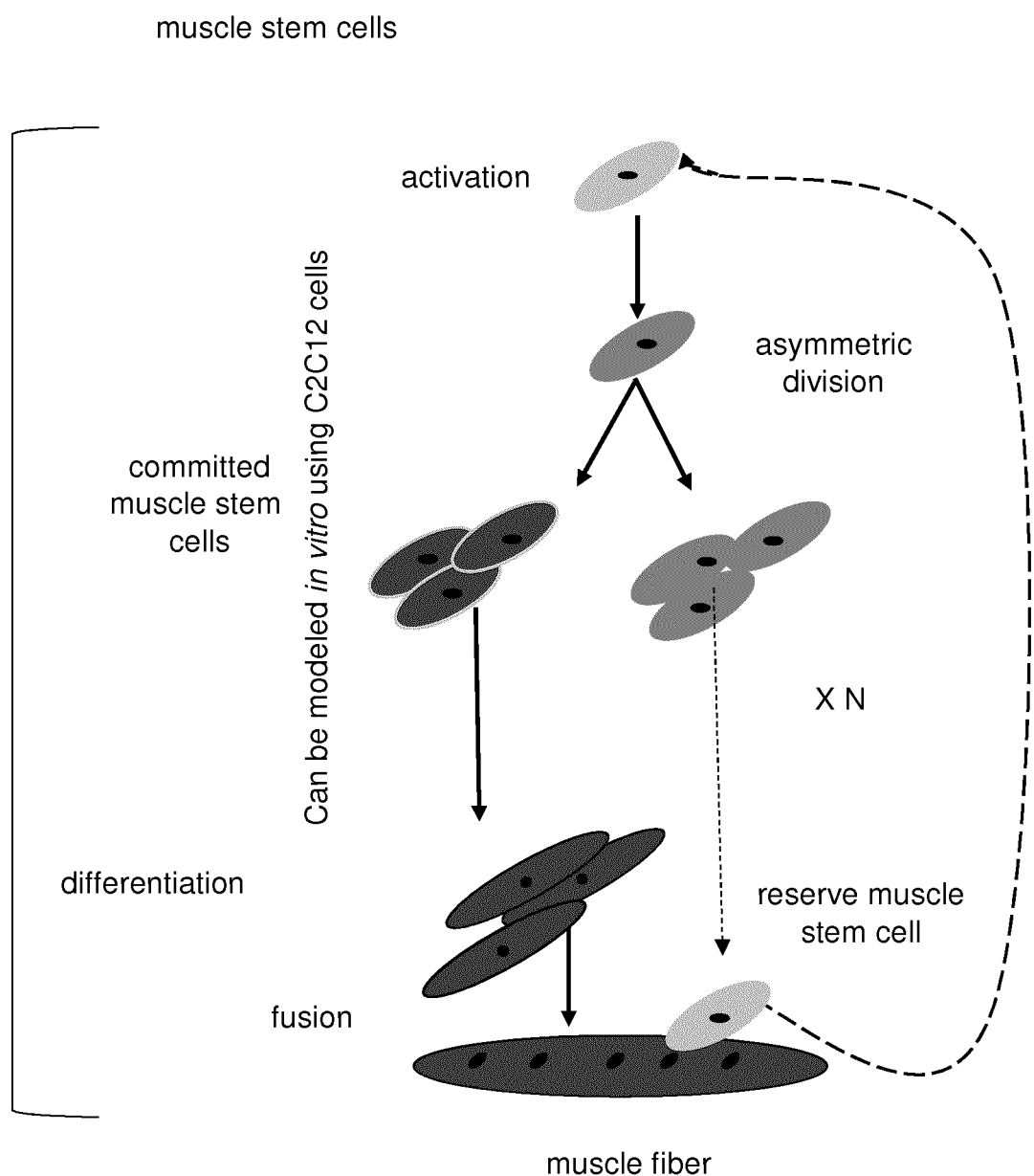
FIG. 1 shows muscle stem cells as a model for muscle aging and regeneration. Multiple rounds of this cycle throughout the life span represent muscle stem cell aging through exhausting regenerative potential and loss of muscle memory. In particular, muscle stem cells undergo several divisions that result in proliferative expansion. A fraction of the dividing stem cells undergoes the self-renewing process and becomes the reserve stem cells. Upon receiving external signals, stem cells differentiate and fuse to form muscle fibers with reserve cells as stem cells [Yaffe and Saxel, 1997]. The reserve cells can undergo this cycle again. Multiple rounds of such cycling and stem cell pool depletion result in aging characteristics. This process can be modeled in vitro using C2C12 cells.

Various apparatuses or processes will be described below to provide an example of an embodiment of each claimed invention. No embodiment described below limits any claimed invention and any claimed invention may cover processes or apparatuses that differ from those described below. The claimed inventions are not limited to apparatuses or processes having all of the features of any one apparatus or process described below or to features common to multiple or all of the apparatuses described below. It is possible that an apparatus or process described below is not an embodiment of any claimed invention. Any invention disclosed in an apparatus or process described below that is not claimed in this document may be the subject matter of another protective instrument, for example, a continuing patent application, and the applicants, inventors or owners do not intend to abandon, disclaim or dedicate to the public any such invention by its disclosure in this document.

Use of stem cells, including for example human stem cells, for treating a wide range of human disorders and diseases in the clinic has been expanding over the last decade, but there are some limitations on these past usages. For example, some limitations may relate to various functional properties of stem cells, such as the ability to proliferate and differentiate efficiently and robustly, to resist cell death and other suppressive signals, which may generally decline as stem cells are being manipulated ex vivo or in vitro.

One challenge with some existing practices involving the use of stem cells for such therapeutic treatments can be the time delay or lag between the provision of the original, young stem cells and their ultimate use in a therapeutic treatment. During this time period, the stem cells can age, which may affect one or more functions of the cell. For example, one or more cell functions of a given stem cell may experience age-associated declines in its function. This can, in some instances, result in the aged stem cells having degraded cell functions which may affect their usefulness and/or effectiveness in the subsequent therapeutic treatment. As described herein, the inventors have discovered a method of preconditioning stem cells, including irradiating a group of untreated, target stem cells, that may help reduce at least some types of age-associated decline of some cell functions as the treated stem cells age, while still leaving the stem cells alive and suitable for use in therapeutic treatment(s). As used herein, the term "preconditioning" can refer to the exposure of stem cells to an agent or stimulus to improve the regenerative and/or functional properties of the cells. For example, stem cells may be preconditioned prior to therapeutic transplantation.

Some protocols have been developed to try and help improve the therapeutic properties of given stem cells that are to be used in such treatments, collectively called preconditioning, have been suggested, including, for example, exposure to hypoxic conditions, growth factors and conditioned medium from other cells. According to literature, these methods may have various degrees of improvements, depending on stem cell types, disease and end-points measured.

However, some of these preconditioning techniques can have limits and/or drawbacks. For example, there have been some indications that preconditioning stem cells with hypoxia may lead to relatively poorer differentiation. Exposure to growth factors may be associated with higher cost of the treatments. Incubating stem cells with conditioned medium may require additional culture of "unaffected" stem cells which in many cases may not be accomplished or does not apply to therapy principle.

Low dose radiation is commonly viewed as an additional health risk factor to the public. However, contrary to this common viewpoint, the inventors have discovered that some cells may benefit from exposure to low dose radiation, and that such exposure may actually improve the desirable, therapeutic properties of the target cells. In particular, as described herein, the inventors have discovered that the low dose radiation as a method to improve existing therapy methods, as compared to some known radiobiology research that focuses on relatively high doses of radiation, and have demonstrated some improvements in the characteristics of stem cells exposed to low doses of radiation.

Based on this discovery, and as an alternative to such conventional preconditioning techniques, the inventors have discovered a method of preconditioning stem cells, for example cells intended for therapeutic transplantation into a patient-recipient or any other potential use, by exposing them to low doses of radiation, such as ionizing radiation emitted from a suitable radiation source. The inventors have discovered that such exposure has been found to help preserve (i.e. slow the deterioration/degradation of) certain cell functions of a given stem cell or group of stem cells, such as cell proliferation, cell viability, tissue specific memory, differentiation potential and other functional properties that are related to efficacy of therapy or to other uses, and may help reduce the degradation of such attributes or functions over time as the stem cells age. This may help the aged, preconditioned stem cells exhibit attributes that are relatively closer to the attributes of young stem cells for longer time periods than non-preconditioned (i.e. control) stem cells of the same type.

This type of preconditioning can, in some instances, be distinguished from other types of modifying and/or attempting to enhance the properties of stem cells beyond the standard, or control properties of untreated, young stem cells. For example, some of the techniques disclosed herein use the unmodified attributes of young stem cells as a baseline/reference and are intended to reduce the degree to which the attributes decline or deviate from these baseline values as the stem cells age, as compared to intending modify the stem cells so that their attributes exceed the baseline functions of the non-treated, young stem cell control group.

That is, the disclosed methods may, for some cells and some functions, reduce the age-associated decline of at least a first cellular function of each target stem cell. For example, a given cellular function may have an initial performance value that can be measured on a group of young (i.e. non-aged) stem cells, and which can be considered to form a baseline or control value for the given function.

Allowing at least some of the target stem cells to age without being treated as described herein can be used to define an aged performance value for the untreated stem cells. This aged performance value can be measured at any suitable point during the aging process, and can be determined at a threshold aging time which can serve as reference time for the purpose of comparing the characteristics of treated and non-treated stem cells. This threshold aging time can be defined by the passage of time (for example may be measure in seconds, minutes, hours and days or the like), or may be defined by other characteristics, such as the number of rounds of passaging or cell passages.

The stem cells that have been preconditioned using the methods described herein can also be allowed to age until reaching the threshold aging time, at which point a measurement of the relevant cell function can establish a treated performance value. It has been discovered by the inventors that treating the cells in the manner described herein can reduce the degradation of at least some cell functions, which can be understood as meaning that the treated performance value remains closer to the control, initial performance value than the aged performance value of the untreated cells (e.g. the aged, treated cells have functionality closer to the original young cells than the aged, non-treated cells). That is, for most measured values, the treated performance that may be between the aged performance value and the initial performance value. In some examples of the methods described herein, the treated performance value may be closer to the initial performance value than it is to the aged performance value.

While some aspects of the methods herein are described with reference to a single cell function and its associated performance values, some uses of the methods herein may help preserve the values of two or more cell functions within a given stem cell. In such cases, different, respective, performance values may be calculated for each cell function being monitored/compared. The effects of the methods on the different cell functions may be analogous (i.e. that the preconditioned cells tend to have better performance values than the untreated, aged control cells), but may have different magnitudes, proportions, relations, etc. based on the nature of the cell function being measured/compared.

Helping to maintain the functionality of the preconditioned stem cells may allow them to be stored for a longer time period before being utilized in a given therapeutic treatment. This may help accommodate travel/delivery times and/or may allow a batch of stem cells to be prepared in advance of when they are required and to be kept on hand until needed. Alternatively, if the treated stem cells are utilized on approximately the same time scale as non-treated cells would have been utilized, they may show exhibit enhance performance and/or efficacy as compared to the non-treated stem cells. This may it also helps expand the cells to relatively large(r) numbers that are suitable for therapy applications. For example, some stem cell therapies may require a minimum number of stem cells to achieve relatively high therapeutic index, and delay in aging may help facilitate the expansion of such cells for longer times and to larger numbers.

As used herein, the term "stem cells" may refer to cells that can differentiate into specialized cells and can self-renew (i.e., divide to produce more stem cells). Various types of stem cells are well known in the art, and are contemplated in the methods disclosed herein. Examples of stem cells include, but are not limited to, muscle stem cells, mesenchymal stem/stromal and progenitor cells (also known as mesenchymal stem cells or mesenchymal stem and progenitor cells), hematopoietic stem and progenitor cells (also known as hematopoietic stem cells) and and endothelial colony forming cells (also known as endothelial stem and progenitor cells.

For example, in accordance with one broad aspect of the teachings described herein, which may be used in isolation and/or in combination with any of the other suitable aspects described herein, the inventors have shown that exposing C2C12 myoblasts to low dose radiation (LDR) may help enhance muscle stem cell memory (i.e. inhibit the age-related decline in muscle stem cell memory function) which may help improve their potential to differentiate into muscle fibers. For example, exposure to LDR may enhance retention of muscle stem cells ability to differentiate and form muscle fibers during extended in vitro growth. This property may help contribute to the successful therapeutic application of muscle stem cells in regenerative medicine and may be inversely related to the length of cell culture and/or aging. The inventors have also shown that markers of myogenic differentiation were increased in cultures of C2C12 myoblasts exposed to LDR compared to unirradiated controls.

Accordingly, this disclosure provides at least one example of a method of preconditioning stem cells comprising exposing stem cells to low dose radiation (LDR), thereby providing preconditioned stem cells having enhance therapeutic properties as compared to similarly aged, and non-preconditioned stem cells.

The attributes and/or therapeutic properties that may be enhanced by LDR preconditioning may include, in some examples, delayed aging of the preconditioned stem cells (as compared to the cell functions of analogous, non-precondition stem cells) and a corresponding delay in aging-associated loss of proliferation. It is noted that this need not include an improvement in the proliferation of relatively young stem cells (i.e. the proliferation of young LDR preconditioned stem cells may not exceed the proliferation of young, non-preconditioned stem cells). Other functional capacities that may be enhance by LDR preconditioning may include, in some examples, enhanced retention of muscle stem cells ability to differentiate and form muscle fibers during extended in vitro growth.

In some embodiments of the teachings described herein, the stem cells may be muscle stem cells. As used herein, the term "muscle stem cell" refers to stem cells present in skeletal muscle tissue, which can self-renew and are capable of giving rise to skeletal muscle cells. Muscle stem cells are also referred to as satellite cells. These stem cells are activated in response to muscle injury to regenerate damaged muscle tissue.

Alternatively, the stem cells to be LDR preconditioned may be mesenchymal stem/stromal and progenitor cells (MSC/MSPCs). MSCs are multipotent stromal cells that can differentiate into a variety of cell types, including, but not limited to: adipocytes, chondrocytes and osteocytes.

In some embodiments, the stem cells to be LDR preconditioned may be endothelial colony forming cells or endothelial stem and progenitor cells. Endothelial colony forming cells may give rise to endothelial cells that line all blood vessels, inner chambers of the heart and lymphatic vessels Optionally, stem cells to be LDR preconditioned may be hematopoietic stem and progenitor cells (HSCs). HSCs may be located in the bone marrow and give rise to all blood cell lineages and platelets.

While experimental data is provided herein for the irradiation of some exemplary types of stem cells, it is expected by the inventors that other types of stem cells, such as cardiac stem cells, may exhibit analogous age-delaying behaviors when preconditioned in accordance with the techniques described herein, including via irradiation with LDR. For example, different stem cells tend to have similar biology and function, i.e., they are quiescent cells that reside in specialized niches and wait for the physiological signals to migrate, divide and differentiate. Since delayed aging effects were demonstrated for 3 different stem cell types with a similar degree of improvement the inventors believe it is reasonable to believe that other stem cells may behave in a similar manner.

As used herein, the term "low dose radiation" (LDR) refers to a dose of low linear energy transfer (LET) ionizing radiation that is similar to, or just above, natural background levels of radiation. Radiation dosages of less than 500 mGy are understood to be low dose radiation levels and, in accordance with the teachings described herein, low dose radiation may be a dose of ionizing radiation of less than about 500, 400, 300, 200, 150, 125, 110, 100, 75, 50, 25, 12 or 10 mGy. In the examples described herein, some particular radiation doses have been demonstrated as helping to inhibit age-related degradation of stem cells.

The low dose radiation described herein may be provided using any suitable irradiation source that can emit low linear energy transfer (LET) ionizing radiation in the dosage ranges described herein. Gamma (γ)- and X-ray radiation are two examples of suitable LET radiation that can be used for preconditioning. As will be understood by a person of skill in the art, LET is an amount of energy deposited into a substance traversed per unit length, i.e. keV/um. Anything below about 10 keV/um can be considered to be low LET for use with the methods described herein (for example γ- and X-ray radiation).

Accordingly, the suitable types of ionizing radiation can include optionally X-ray or γ-radiation. In one embodiment of the methods described herein, the ionizing radiation may be γ-radiation, and in another embodiment, may be X-ray radiation. In the described methods, the stem cells may be exposed to radiation in doses of between about 1 and about 500 mGy of radiation, and in some examples, may be between about 2 and about 200 mGy, between about 10 and about 150 mGy of radiation, between about 10 mGy and about 100 mGy. In some preconditioning processes, the target stem cells may be exposed to about 10 mGy, 50 mGy and/or about 100 mGy of ionizing radiation. In other embodiments, the stem cells may be exposed to 8 to 12 mGy of radiation, optionally 10 mGy of radiation or 90 to 110 mGy of radiation, and optionally 100 mGy.

Sources of γ-radiation for exposing stem cells to LDR include, but are not limited to, $^{60}$Co and $^{137}$Cs, which can be used for medical purposes. In another embodiment, stem cells are exposed to LDR from an X-ray irradiator.

The stem cells may be irradiated (i.e. exposed to LDR) for preconditioning through any suitable method, including those described herein. The stem cells may optionally be exposed to LDR in vitro or ex vivo.

In some embodiments of the methods described herein, the cells to be LDR preconditioned may be in cell culture at the time of their preconditioning/exposure. For example, a population, or culture, of stem cells in a Petri dish or a test tube may be exposed to LDR.

Exposure times for irradiation, to achieve a desired level of preconditioning of a given stem cell can vary. The irradiation time for a given stem cell may be selected based on a variety of factors including, for example, the desired dose of LDR, the method of irradiation and available instrumentation. In some applications, the time of exposure may vary between 1 s and 24 h. In one embodiment, the stem cells are exposed to LDR for 1 s-10 min.

In one embodiment, the aged stem cells that have been exposed to LDR have improved (i.e. less degraded) properties compared to aged stem cells that have not been exposed to LDR. These improved properties may include, but are not limited to, improved regenerative properties, increased or improved differentiation potential, increased viability, increased proliferation, increased therapeutic efficacy, and increased preservation of stem cell properties. These properties may be assessed by any suitable method. Any of the attributes/properties may be increased by at least 10, 25, 50, 75, 100, 200 or 300% compared to stem cells that have not been exposed to LDR.

For example, in embodiments where the stem cells are muscle stem cells, the aged muscle stem cells that have been exposed to LDR have shown increased differentiation into muscle fibers as compared to aged muscle stem cells that were not been exposed to LDR (that is, may have degraded less from the young cell control values than the untreated muscle stem cells).

Methods for assaying differentiation into muscle fibers are known in the art, and can involve quantifying the fraction of stem cells that become parts of newly formed muscle fibers.

For example, in one embodiment, a muscle fiber differentiation assay is used. In this example, a fusion index is calculated using the formula: $I_f = N_{fused}/N_{total} \times 100\%$, where $N_{fused}$ is the number of nuclei with myosin-positive cells (i.e., muscle fibers) and $N_{total}$ is the total number of nuclei scored. A higher fusion index indicates increased differentiation into muscle fibers. Accordingly, in one embodiment, the muscle stem cells that have been exposed to LDR have a higher fusion index after at least 5, 10, 15, 30, 60 or 90 days of culture following the exposure, or within about 1 to about 100 days of culture following irradiation, as compared to muscle stem cells that have not been exposed to LDR.

In other embodiments, stem cells that have been exposed to LDR may have higher expression of at least one marker associated with cell differentiation compared to stem cells that have not been exposed to LDR. For example, where the stem cells are muscle stem cells, the muscle stem cells that have been exposed to LDR may have higher expression of at least one marker associated with muscle cell differentiation compared to muscle stem cells that have not been exposed to LDR. Markers of muscle differentiation are can include, but are not limited to, myogenin, MyH3, MyoD, TKS5 and TMEM8c. Accordingly, in one embodiment, the muscle stem cells that have been exposed to LDR have increased gene or protein expression of a marker of muscle differentiation, optionally myogenin, MyH3, MyoD, TKS5 and/or TMEM8c, after at least 5, 10, 15, 30, 60 or 90 days culture following the exposure to LDR compared to muscle stem cells that have not been exposed to LDR. Many myogenic pathways may be activated in the treated muscle stem cells confirmed by next generation gene expression sequencing.

In some embodiments, the method can include obtaining or providing stem cells prior to exposing them to LDR. For example, the stem cells may be harvested from a tissue sample. As used herein, a "tissue sample" may be any sample of tissue that contains a stem cell. The tissue sample may be obtained from any mammal, including, but not limited to, humans and mice. In one embodiment, the tissue is muscle. As used herein, the term "harvesting cells" refers to isolating or extracting cells from a tissue sample such as muscle. Suitable methods of harvesting cells from tissue samples are known in the art.

The stem cells used in the methods herein may be from any suitable source, and may be generated from other cell types. For example, embryonic stem cells (ESCs) and induced pluripotent stem cells (iPS) may be converted to muscle stem cells (Maffioleti et al., 2015 and Chal et al., 2015).

The stem cells may be grown and/or maintained in cell culture prior to, during and/or after exposure to LDR. As is commonly understood in the art, cell culture is the process by which cells are grown under controlled conditions, generally outside of their natural environment. Normally, cells in culture are maintained in culture media. As used herein, the term "culture media" refers to media designed to support the growth of cells, in particular stem cells. Various culture media are known in the art. In one embodiment, the culture media is a basal media such as Dulbecco's modified Eagle's medium (DMEM), advanced DMEM, Biogro™, SkGM™, Ham's F10, Ham's F12, Iscove's modified Dulbecco's medium, neurobasal medium, RPMI 1640 or MCDB120 medium. The medium may contain serum or be serum-free. In one embodiment, muscle stem cells are grown in DMEM with 10% FBS and differentiated to form muscle fibers in DMEM containing 2% Horse Serum, 5 µg/ml Insulin and transferrin.

Optionally, the harvested stem cells are maintained in culture for at least 1, 2, 3, 4, 5, 6, 7, 8, 9 or 10 or more passages, optionally 3 passages, prior to exposure to LDR.

In other embodiments, the method further comprises administering the preconditioned stem cells to a subject in need thereof.

Populations of Preconditioned Stem Cells

This disclosure also provides a cell population (for example, a cell culture), comprising stem cells that have been exposed to LDR. In one embodiment, the cell population comprises preconditioned stem cells obtained by the methods described herein. As used herein, the term "cell" refers both to a single cell and a plurality of cells. A "plurality of cells" may include a cell population.

Optionally, the preconditioned stem cells in the population can be preconditioned muscle stem cells. Alternatively, the preconditioned stem cells in the population may be mesenchymal stem/stromal and progenitor/cells or are endothelial colony forming cells/endothelial stem and progenitor cells. In yet another example, the preconditioned cells in the population may be hematopoietic stem and progenitor cells. The preconditioned stem cells may optionally be human stem cells.

Pharmaceutical Compositions

In accordance with another broad aspect of the teachings described herein, pharmaceutical compositions may be created that include a preconditioned stem cell, created using the methods described herein, in as an active ingredient along with a suitable, pharmaceutically acceptable carrier.

As used herein, the term "pharmaceutically acceptable carrier" is intended to include any and all solvents, dispersion media, coatings, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Optional examples of such carriers or diluents include, but are not limited to, water, saline, Ringer's solutions, dextrose solution, and 5% human serum albumin.

A pharmaceutical composition may be formulated to be compatible with its intended route of administration. Examples of routes of administration include parenteral, e.g. intravenous, intradermal, subcutaneous, oral (e.g. inhalation), transdermal (i.e., topical), transmucosal, and rectal administration.

The active ingredient may be prepared with a carrier that will protect it against rapid elimination from the body, such as a sustained/controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Optionally, oral or parenteral compositions may be formulated in dosage unit form for ease of administration and uniformity of dosage. Dosage unit form as used herein refers to physically discrete units suited as unitary dosages for the subject to be treated; each unit containing a predetermined quantity of active ingredient calculated to produce the desired therapeutic effect in association with the required pharmaceutical carrier. The specification for the dosage unit forms may be dictated by and depend on the unique characteristics of the active ingredient (i.e. preconditioned stem cell) and the particular therapeutic effect to be achieved, and the limitations inherent in the art of preparing such an active ingredient for the treatment of individuals.

The formulation may also contain more than one active ingredient as necessary for the particular indication being treated, optionally those with complementary activities that do not adversely affect each other. Alternatively, or in addition, the pharmaceutical composition can comprise an agent that enhances its function. Such molecules are suitably present in combination in amounts that are effective for the purpose intended.

Uses of Preconditioned Stem Cells

Populations of preconditioned stem cells can be obtained according to the methods described herein. Applications and uses of preconditioned stem cells may include, but are not limited to, preservation of stem cell properties during expansion, differentiation of stem cells into particular lineages (for example, differentiation of muscle stem cells into muscle fibers) and tissue regeneration. The differentiated lineages can be used for both in vitro or in vivo purposes.

The preconditioned stem cells and pharmaceutical compositions described herein may be useful for treating or preventing a disease or condition. Some examples of diseases or conditions that may be treated using some type preconditioned stem cell(s), optionally those described herein, may include muscular dystrophy, sarcopenia, Type 2 Diabetes, Septic Shock, multiple sclerosis, knee osteo arthritis, acute graft versus host disease, heart failure, Crohns disease, acute myocardial infarction, acute myocardial infarction, pulmonary hypertension, and critical limb ischemia.

Preferably, the disease or condition is a disease or condition known to benefit from stem cell therapy. For example, the preconditioned muscle stem cells and pharmaceutical compositions described herein may be useful for treating or preventing a muscle disease or muscle condition.

The preconditioned muscle stem cells and pharmaceutical compositions described herein may optionally be used in a method for treating or preventing a muscle disease or condition, the method comprising administering an effective amount of a preconditioned muscle stem cell or pharmaceutical composition disclosed herein to a subject in need thereof.

Optionally, an effective amount of a preconditioned muscle stem cell or pharmaceutical composition disclosed herein may be used for treating or preventing a muscle disease or condition.

Optionally, the muscle disease or condition may be a genetic disease (for example, Duchenne muscle dystrophy or facioscapulohumeral muscular dystrophy). In another embodiment, the muscle disease or condition is an aging-related muscle disease (for example, sarcopenia). In another embodiment, the muscle disease or condition is a muscle injury. In yet another embodiment, the muscle disease or condition is non-genetic or aging related (for example, cachexia associated with cancer, kidney failure, chronic obstructive pulmonary disease or other).

As used herein, the term "subject" may include any suitable members of the animal kingdom, including, for example, mammals and in particular a human being. For example, the subject may be a patient having a disease or condition, such as a muscle disease or condition.

The preconditioned stem cells may be autologous stem cells (i.e., stem cells originating from the subject), or may be allogeneic stem cells (i.e., stem cells not originating from the subject).

An effective amount of a preconditioned stem cell or pharmaceutical composition of the disclosure relates generally to the amount needed to achieve a therapeutic objective. Efficaciousness of treatment may be determined in association with any suitable method for diagnosing or treating the disease. Alleviation of one or more symptoms of the disease indicates that the preconditioned stem cell or pharmaceutical composition may confer a clinical benefit.

As used herein, "treating or preventing" includes, but is not limited to, reversing, alleviating or inhibiting the progression of the disease or condition or symptoms or conditions associated with the disease or condition. Preventing includes preventing occurrence of the disease or condition or symptoms or conditions associated with the disease or condition or preventing worsening of the severity of the disease or condition or symptoms or conditions associated with the disease or condition. Accordingly, "treating or preventing the disease or condition" optionally includes the prophylactic treatment of a subject to prevent or reduce the incidence or recurrence of the disease or condition or symptoms or conditions associated with the disease or condition.

Methods of administering stem cells to a subject are known in the art. For example, the preconditioned stem cells or compositions described herein may be administered systemically or locally to a specific site or tissue of interest. In one embodiment, the preconditioned stem cells or compositions described herein are injected into a subject. In another embodiment, preconditioned muscle stem cells are injected into muscle.

The preconditioned stem cells or compositions described herein may be used or administered in combination with another stem cell therapy or cell therapy. In this manner, the preconditioned stem cells or compositions described herein may be used to augment the therapeutic capacity of non-irradiated cells.

The following non-limiting examples of methods of preconditioning some examples of stem cells.

Example 1

Low doses of X-rays and γ-radiation have been shown to produce various stimulatory effects at cellular and organismal levels, collectively termed radiation hormesis or radiation homeostasis [Calabrese, 2015; Calabrese, 2016; Baldwin and Grantham, 2015; Jolly and Meyer, 2009]. Previous results demonstrated that low dose radiation (LDR), and specifically low-dose γ-radiation, may delay the onset of tumorigenesis in vivo [Mitchel et al., 2003; Mitchel., 1999] and inhibit aging-related accumulation of DNA lesions in vivo [Osipov et al., 2013]. Very little is known about the effects of LDR on stem cells. The results of a few studies that examined the effects of LDR on stem cells are inconsistent. The inventors have discovered that the therapeutic properties of mouse and human muscle stem cells can be enhanced by preconditioning the muscle stem cells using LDR.

C2C12 mouse muscle myoblasts, a cell model commonly used in muscle stem cell biology, were used to study the effects of LDR on muscle stem cells. The results show that LDR exposure of C2C12 cells improves muscle fiber formation by these cells and that loss of this capacity, routinely observed in a long-term culture, is partially reversed as a result of LDR exposure of young cultures, as compared to unirradiated controls.

Methods

C2C12 Mouse Muscle Stem Cells

These cells, also called myoblasts and originally derived from the hind limb muscle of adult C3H mouse, were purchased from ATCC. C2C12 myoblasts are efficiently fusing sub clone of C2 myoblasts and have been used extensively as a model for muscle differentiation and muscle stem cell biology in tissue culture. For growth, cells were maintained in Dulbecco's modified media (4.5 g/L glucose) supplemented with 10% fetal calf serum, 4 mM L-Glutamine, and 1.5 g/L sodium bicarbonate while not allowing cell density to achieve greater than 80% confluency.

Human Biopsy Derived Muscle Stem Cell Culture

Muscle biopsy derived stem cells were purchased from a biotech company Lonza. To attain an exponentially growing culture, cells were maintained in skeletal muscle basal medium supplemented with 20% FBS (fetal bovine serum), 4 mM L-Glutamine, Gentamycin, human EGF (epidermal growth factor), Dexamethasone and 1.5 g/L sodium bicarbonate while not allowing cell density to achieve greater than 80% confluency.

Long-Term Culture

Muscle tissue regeneration, a continuous process that goes on throughout an organism's life span, implies multiple rounds of successive changes between proliferation mode (myoblasts), differentiation and self-renewal, and stand-by or reserve mode (FIG. 1). To model this in vitro, C2C12 myoblasts (proliferation mode) can be stimulated to differentiate and self-renew, followed by a release of self-renewed stand-by cells, also called reserve cells, back into proliferation mode [Yaffe and Saxel, 1997]. Multiple rounds of these changes represent an in vitro model of exhausting myogenic potential of muscle stem cells (FIG. 1). This decline may mimic changes that occur in satellite cells under in vitro expansion conditions. Reserve cells exhibit many classical features of satellite cells, such as asymmetric stem cell division, higher expression of markers of specification such as Pax7 and potential for differentiation. Functional properties of muscle stem cells undergoing multiple rounds of differentiation-proliferation would decline with the number of such rounds. Reserve cells were obtained from differentiated muscle fiber culture by performing differential enzymatic digestion.

Unlike C2C12 myoblasts described herein, freshly isolated muscle stem cells from muscle biopsy may have limited (10-12) doubling capacity. Therefore, instead of performing reserve cell isolation, muscle stem cells were maintained in growth media for 14 days and 3 days in differentiation media.

Differentiation of C2C12 Muscle Cells into Muscle Fibers

Cultures grown to 80-90% confluency in growth medium were washed twice with phosphate buffer saline and incubated in differentiation medium (DM:DMEM with 2% horse serum and antibiotics). DM was replaced every day until the end-points were reached. Incubation in DM medium triggers the process of differentiation, an essential part of which is the fusion of myoblasts into multinucleated muscle fibers. By 72 h of differentiation approximately 50-70% of myoblasts are fused into muscle fibers.

Differentiation of Human Muscle Stem Cells into Muscle Fibers

Cultures grown to 80-90% confluency in growth medium were washed twice with phosphate buffer saline and incubated in differentiation medium (DM:DMEM-F12 1:1 with 2% horse serum and antibiotics).

Irradiation

Figure 2:
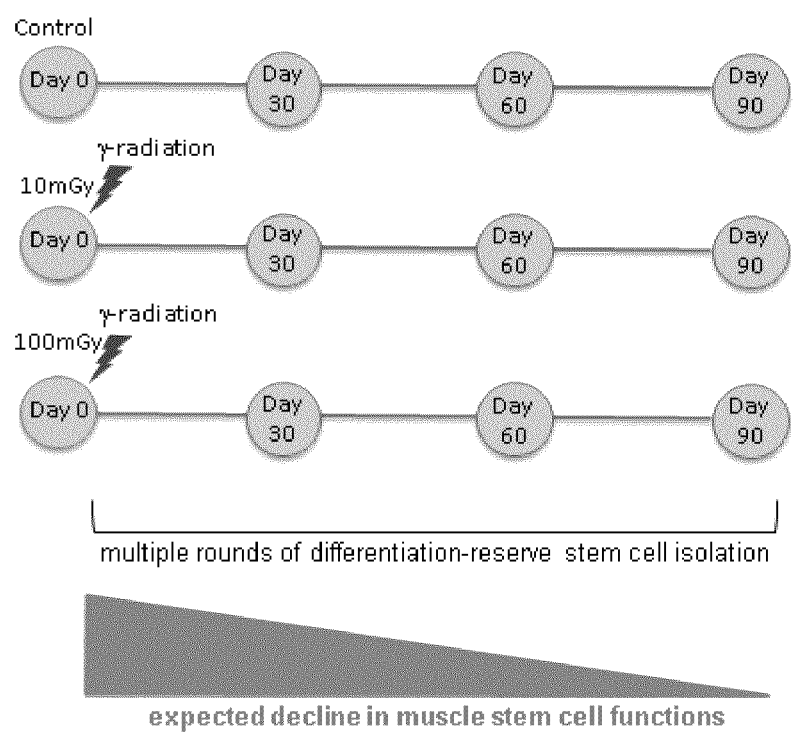
FIG. 2 shows an experimental design. C2C12 myoblasts were exposed to LDR (0, 10 or 100 mGy) and maintained via consecutive cycles of differentiation and isolation of reserve cells (as described in FIG. 1) for 30, 60 and 90 days.

In the present example, young C2C12 myoblasts were irradiated with 10 or 100 mGy or sham-irradiated using a Gamma-Cell 200 device equipped with a $^{60}$Co source. Following irradiation, cells were maintained for up to 90 days in culture as described in the "Long-term culture" sub-section (FIG. 2). At time-points 30, 60 and 90 days, cells were assayed for proliferation and differentiation end-points.

Young human biopsy derived muscle stem cells were irradiated with 10 or 100 mGy or sham-irradiated using a Gamma-Cell 200 device equipped with a $^{60}$Co source. Following irradiation, cells were maintained for up to 14 days in culture as described in the "Long-term culture" sub-section. At the end of 14 days cells were shifted to differentiation media to obtain muscle fibers and assayed for differentiation and fusion index.

Muscle Fiber Differentiation Assay

Cultures on glass coverslips, that have undergone differentiation for various periods of time, were fixed in 4% paraformaldehyde and immunolabelled with a primary anti-MyH3 antibody (Myosin Heavy Chain) diluted in PBS/5% BSA solution overnight at 4° C. After washing, cells were incubated with a secondary antibody conjugated with Alexa Fluor 488 (Invitrogen-A11001). Prior to visualization, coverslips were mounted in mounting medium with DAPI (Vector Laboratories Inc. H-1500). Images were taken using a Zeiss Epifluorescence Observer Z1 microscope under 40× magnification.

The fusion index was calculated using the formula:

$$I_f = N_{fused}/N_{total} \times 100\%,$$

Where:
$N_{fused}$ is the number of nuclei within myosin-positive cells (muscle fibers) and
$N_{total}$ is the total number of nuclei scored.
In total, 500 nuclei were scored per sample.

Western Blot

Whole cell lysates were prepared from differentiated C2C12 muscle fibers as follows. Cell pellets were resuspended in 1 pellet volume of modified buffer C (20 mM Hepes pH 7.6, 1.5 mM MgCl$_2$, 650 mM KCl, benzonase (2.5 units/10$^7$ cells), 0.2 mM PMSF, 0.5 mM DTT, 5 mM β-glycerolphosphate, and 1 mM sodium orthovanadate) and centrifuged for 30 min at 4° C. Homogenates were then diluted with 1 pellet volume of Buffer E (20 mM Hepes pH 7.6, 1.5 mM MgCl$_2$, 0.2 mM EDTA, 1 mM PMSF, 0.5 mM DTT, 5 mM β-glycerolphosphate, and 1 mM sodium orthovanadate). Extracted proteins were then recovered from the cells by centrifugation at 15,000×g for 30 min at 4° C. Extracts were quantitated for protein concentration prior to SDS PAGE. Each quantified extract was loaded and resolved in a gradient polyacrylamide gel and transferred to PVDF membrane for western blot analysis. Antibodies were purchased from Santa Cruz Biotechnologies (MyoD, SC 304; Myogenin, S.C. 12732; Myh3, SC 53091 and Tubulin, S.C. 23948).

Quantitative RT-PCR

Cell cultures were trypsinized and pellets were produced by centrifugation. RNA was isolated from cultured cells using Qiazol (Qiagen). Attached cultures were washed once with cold PBS, residual PBS was removed and cells were scraped into Qiazol (1 mL for 4×10$^6$ cells and 0.5 mL for 2×10$^6$). The lysate was vortexed vigorously to shear genomic DNA and then stored at −70° C. until further processing. RNA was purified following manufacturer's instructions (Invitrogen). Briefly, samples were thawed at room temperature for 5 min, 200 µL chloroform per mL of Qiazol was added, vortexed vigorously for 30 sec, and phases were separated by centrifugation at 12000 rpm. RNA in the aqueous phase was carefully removed and processed using mi RNeasy mini kit (Qiagen cat #217004). Finally RNA was dissolved/eluted in nuclease free water (Eppendorf) and tested for quality and quantity using a Nanodrop spectrophotometer and Experion. 2.5 µg of total RNA was used to generate cDNA (RT first strand Kit Qiagen cat #330404). cDNA was diluted 1:5 in H$_2$O and mixed with Sybr green master mix (2×SYBR Biotool) and 2.5 pico moles of primer. Analysis was done in triplicate using the 7900HT Sequence Detection Systems cycler (BioRad) and the CFX manager software. Primers used in the quantitative RT-PCR were designed by Primer 3 software and checked by BLAST (Basic Local Alignment Search Tool) analysis. Primer sequences used in this study are listed as follows, Myogenin Forward GGC TCA AGA AAG TGA ATG AGG C; Myogenin Reverse CGA TGG ACG TAA GGG AGT GC; Myh3 Forward GCATAGCTGCACCTTTCCTC; Myh3 Reverse GGC CAT GTC CTC AAT CTT GT; TKS Forward CTT TGT GGG GAA GAT GCT CG; TKS5 Reverse TCC TTC TGG CCA CCT TCA AT; TMEM8C Forward GCT CCT ATG CAA AGA CTG GC; TMEM8C Reverse GGT CGA TCT CTG GGG TTC AT.

RNAseq 60 days old mouse muscle (C2C12) cell cultures were trypsinized and pellets were produced by centrifugation. RNA was isolated and purified following manufacturer's instructions (Invitrogen), as described in herein. Purified RNA was later subjected for quality control. 5 µg RNA used in library preparation and 75 base pair single end sequencing performed as per standard illumina procedures for the Next Seq 500 genome sequencer. RNAseq data were analyzed using the Bowtie, Tophat2 Cuffdiff (CuffLinks v1) software suit. Sequencing reads were mapped to GRC m38 mouse genome assembly with HISAT2 v2.0.4, guided by GEN- CODE vm12 gene expression model. Identification and quantification of differently expressed genes were performed using Cuffdiff and data sets presented as a Venn diagram. Functional relevance of differentially expressed genes in the LDR (10 and 100 mGy) treatment group were interpreted using a Gene Ontology (GO) pathway analysis software which specifically consider biological processes (BP).

Statistical Analyses

All experiments except RNAseq were repeated three times from the stage of tissue culture initiation and LDR exposures, so they represent biological replicates. Mean values from the three replicates were calculated. Statistical significance while comparing groups was determined using the Student t-test at $P<0.05$.

Results

LDR Improves the Potential of C2C12 Cells to Differentiate into Muscle Fibers

The potential of C2C12 myoblasts to form muscle fibers at various time-points during the long-term culture experiment and how this potential may be affected by LDR was evaluated. The capacity to form muscle fibers represents an important functional characteristic of muscle stem cells. It can be robustly measured experimentally by maintaining myoblasts under differentiating growth conditions for several days and then quantifying the fraction of myoblasts that became parts of newly formed muscle fibers. This is done by immunofluorescence microscopy, wherein muscle fibers are stained with MyH3 and the nuclei within the fibers are quantified relative to the total number of nuclei (FIG. 3). The resulting fraction of nuclei that are parts of muscle fibers is called a fusion index.

It was found that in the control non-irradiated culture the fusion index (i.e. the control fusion index) drastically decreased in a time-dependent manner from 50% in young cells to less than 3% in 90-day old cells (FIG. 3). If myoblasts were irradiated with 10 or 100 mGy at the beginning of the culture experiment, the decline in the fusion index was not as pronounced as in the non-irradiated culture. The fusion index was higher in both 10 and 100 mGy irradiated cells (i.e. the treated fusion index) compared to the control ones at 30, 60 and 90 days (FIG. 3). Exposure of young myoblasts to LDR delayed their functional decline resulting in 2-5 fold higher potential to form muscle fibers at advanced culture ages.

In this example, a treated fusion index was consistently greater than the aged fusion index (indicated as the UT bars in FIG. 3) at each of the threshold age measurement points (30, 60 and 90 days in this example), and was in some instances at least twice the aged fusion index—and had values of at least 10%, 20% and 30% or more of the initial fusion index.

LDR Improves the Potential of Human Muscle Stem Cells Differentiate to Muscle Fibers In addition to mouse muscle myoblasts, experiments were performed on human muscle biopsy derived stem cells. It was observed that if the muscle stem cells were irradiated to form an irradiated culture, that the fusion index of the irradiated culture (i.e. the treated fusion index) was greater than the fusion index of a control culture comprising untreated/unirradiated muscle stem cells (i.e. the control fusion index). For example, referring to FIGS. 7A and 7B, if muscle stem cells were irradiated with 10 or 100 mGy at the beginning of the experiment and age them in culture for 14 days followed differentiation for 3 days, as exemplified in FIG. 7A, irradiated culture showed increased fusion index by a factor of about 2.5 fold compared to the untreated (unirradiated) control stem cells (as shown, for example in FIG. 7B). In the illustrated example, the treated fusion index was greater than the aged fusion index and was more than about 70% of the initial fusion index (control) for both the 10 mGy and 100 mGy radiation doses.

Mechanisms of Longer Retention of Muscle Identity in LDR Exposed Myoblasts

To examine whether the enhanced muscle fiber formation in LDR-exposed myoblast cultures of advanced ages was due to canonical muscle differentiation pathway, several classical markers of terminal differentiation were quantified by western blot analysis in total protein extracts. These were myogenin, Myh3 (myosin heavy chain) and MyoD. Myogenin and MyH3 showed a considerable reduction upon long-term culture in the control group, whereas marked increases in these protein levels were found in irradiated cells (compare 60 and 90 days for 10 and 100 mGy groups with the age-matched controls in FIG. 4A).

In this example, the preconditioned stem cells can achieve a higher confluency after a given time (10 hrs in this case) than the untreated cells (For the first sample max confluency increase observed was from 67.9% (untreated) to 78.6% (treated). For the second sample max increase was from 61.9% (untreated) to 77.2% for treated). That is, the treated stem cells may take a shorter time to reach a given target confluency, and/or may reach a higher level of confluency in each time than the comparison, untreated cells.

Figure 4:
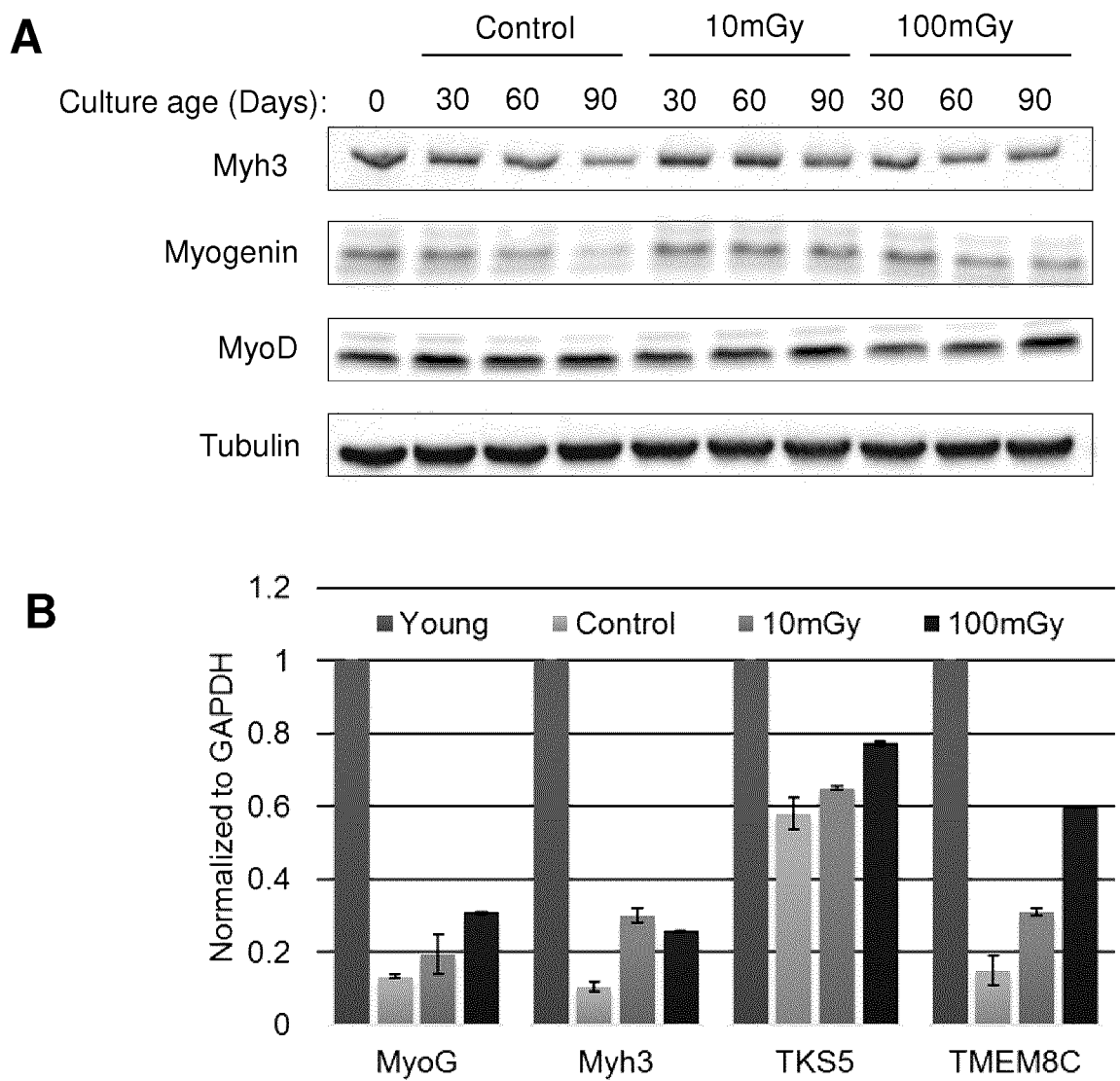
FIG. 4 shows that LDR exposure restores the levels of myogenic proteins and genes in muscle fibers formed by long-term cultures of C2C12 myoblasts. A: Untreated control and irradiated (10 and 100 mGy) cultures of various ages, as well as young cells were incubated in 2% horse serum for 72 hrs to form myotubes. Western blot analysis on whole cell lysates showed a reduction in Myogenin and Myh3 in the untreated control, but levels partially recovered in the irradiated cells. B: Sixty day old cultures of untreated control and irradiated cells (10 and 100 mGy), as well as young cells were incubated in 2% horse serum for 48 h. RNA was extracted and RT-qPCR analysis was carried out to quantify mRNA levels of various gene markers of myogenic differentiation and fusion. Data shows a sharp reduction with time of culture in differentiation markers Myogenin and Myh3 and fusion genes TKS5 and TMEM8c (Myomaker) in the untreated control, but mRNA levels partially recovered in the irradiated cells. Values are means of three technical replicates of a single experiment +/−SD.

These observations were confirmed in an independent experiment in which 60 day old cultures were differentiated and the expression of several genes, that are markers of differentiation and fusion, were assessed by quantitative RT-PCR (see, for example, FIG. 4B).

In addition, referring also to FIG. 5, a comprehensive gene expression analysis using RNAseq of mouse muscle cells at day 60 strengthened the already made observations. In the 10 and 100 mGy irradiated mouse muscle cells, the markers of differentiation and fusion are improved when compared to un-irradiated control, as shown, for example, in Table 1.

TABLE 1

| Gene Name | Muscle Fibers [Myotubes] 10 mGy | | Muscle Fibers [Myotubes] 100 mGy | |
|---|---|---|---|---|
| | Fold Change | p Value | Fold Change | p Value |
| Adam12 | 3.38 | 3.31E−12 | 2.14 | 3.05E−08 |
| Actc1 | 2.76 | 2.18E−10 | 3.21 | 0 |
| Adamtsl3 | 3.26 | 0 | 1.98 | 1.38E−11 |
| Tnnt2 | 0.88 | 0.000857 | 0.74 | 1.80E−05 |
| Myog | 1.86 | 1.39E−07 | 1.43 | 1.96E−09 |
| Tmem8c | 1.37 | 0.000243 | 1.11 | 1.42E−05 |
| ID3 | 2.008 | 9.07E−05 | 1.22 | 0.27756 |
| Igf1 | 1.43 | 5.51E−06 | 1.39 | 1.70E−08 |
| Igfbp3 | 2.56 | 1.13E−07 | 1.31 | 0.000422 |

Figure 6A:
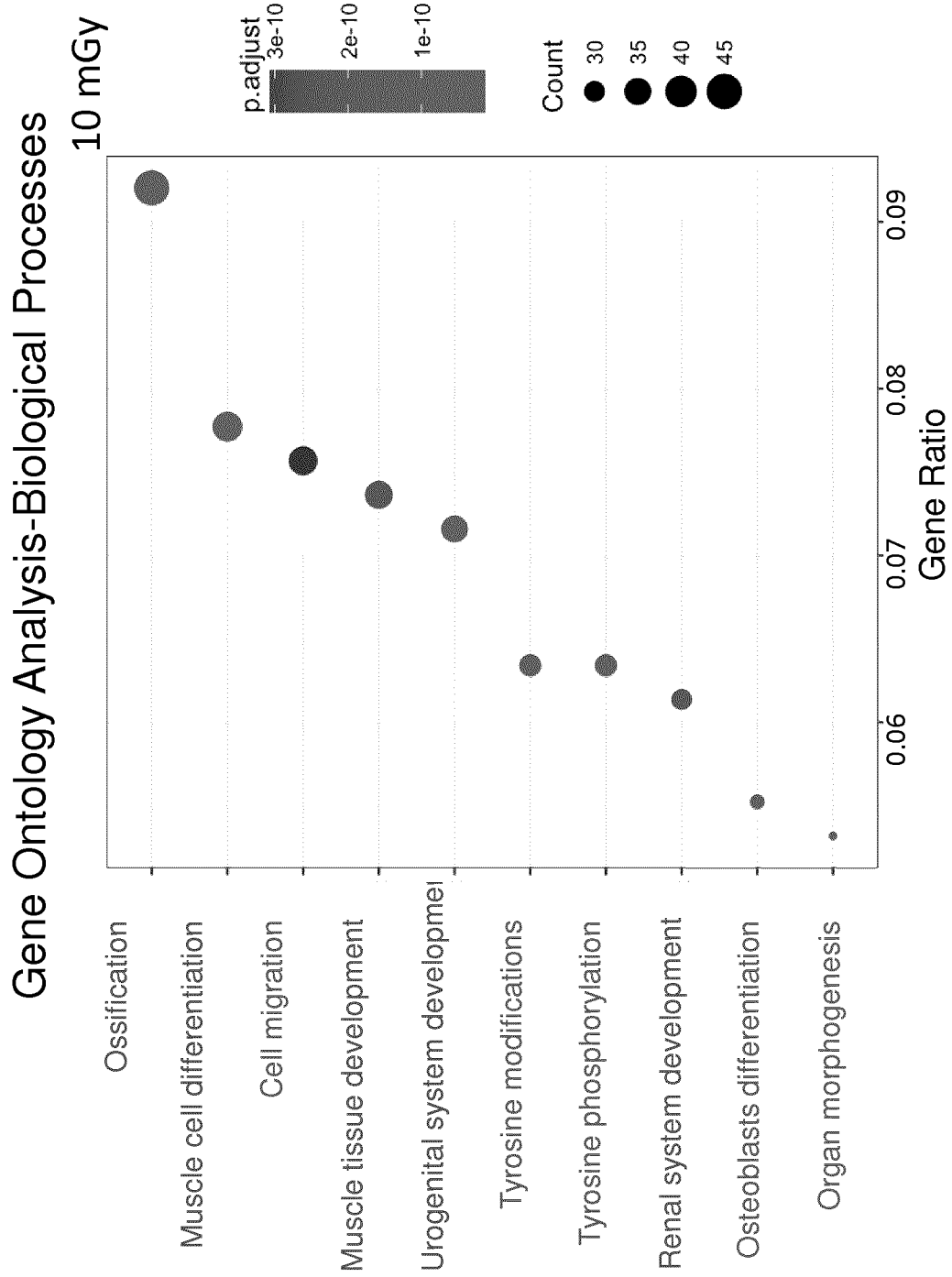
FIGS. 6A and 6B are graphs showing the gene ontology analysis on differentially expressed genes from the venn diagram in FIG. 5B. Treated cells showed higher expression of genes required for muscle fiber formation via myogenic pathways and processes, refer table 1.
Figure 6B:
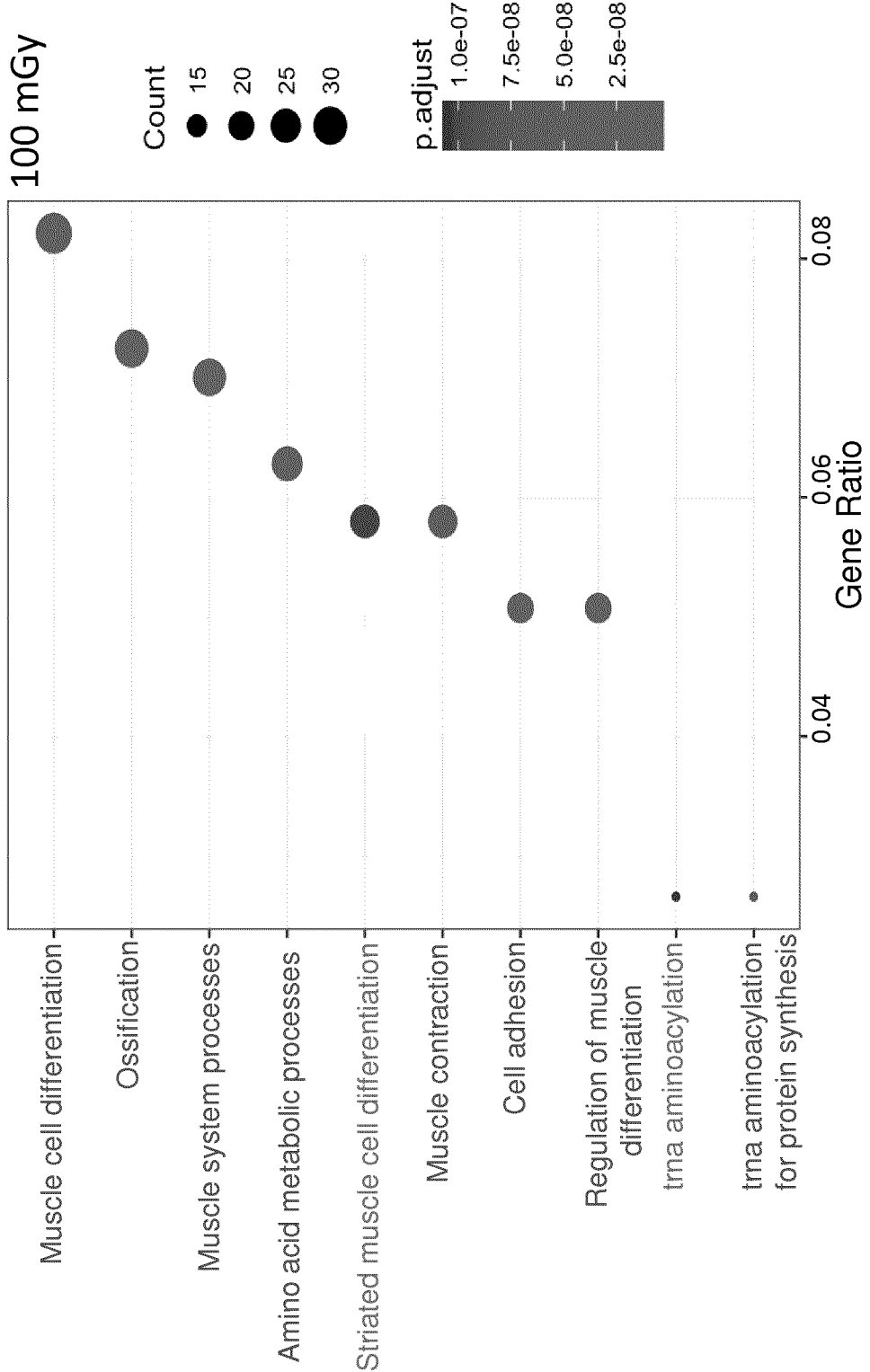

Presented fold changes of gene expression were obtained after normalizing with control myotubes The gene list obtained from data analysis suggests an improvement of muscle fiber formation. Majority of genes differentially expressed in 10 mGy and 100 mGy have decisive functions in differentiation, muscle tissue development, skeletal muscle fiber formation and muscle contraction, as shown in FIGS. 6A and 6B respectively.

Discussion

The retention of the capacity of C2C12 myoblasts normally declines with time/cell age in culture and with the number of differentiation cycles. However, utilizing the methods described herein, the retention of the capacity of C2C12 myoblasts has been enhanced by exposing the cultures to LDR. The observed 2.5 fold improvement of differentiation the human muscle stem cells, underscore at least some of the beneficial effects of low dose radiation in the preconditioning of stem cells (FIG. 7). Noteworthy, limited doubling capacity of human muscle stem cells was a basis to restrict the described culture to 14-17 days rather than the extended 90 days in the immortal C2C12 mouse muscle cells.

Here, it was found that LDR (10 or 100 mGy) improved the differentiation capacity of C2C12 cultures that were subjected to multiple rounds of growth→differentiation-→reserve cell fractionation. A decrease (16-fold) in the fusion index in the control unirradiated cells associated with the length of culture or with the number of differentiation rounds was found. This decline was partially reversed when cells were exposed to LDR at day 7 of culture. Noteworthy, the magnitude of the improvement increased with time (from ~50% at 30 days to >300% at 90 days—FIG. 3B), indicating that the effect of LDR exposure may be maintained for long periods of time.

However, next generation gene expression sequencing performed in 60 days old mouse muscle cells not only showed induction of myogenic markers in 10 and 100 mGy treated cells, but, referring to FIG. 5, also showed several classes of genes involved in muscle fiber formation, muscle tissue development and muscle cell migration required for myogenic fusion and maturation, as shown also in FIGS. 6A and 6B.

It was further confirmed that classical markers of myogenic differentiation were increased in cultures that were subjected to LDR compared to unirradiated controls, suggesting that the LDR may trigger molecular changes that ultimately converge on the canonical pathway of muscle fiber formation. Without being bound by theory, it is believed that these changes could include mechanisms of retention of muscle stem cell identity. For example, regulation of the myogenic differentiation-specific gene expression by histone H3.3 variant may be one such mechanism [Ng and Gurdon, 2008]. This possibility is in line with reports showing that LDR may lead to epigenetic chromatin rearrangement (reviewed in [Miousse et al., 2017]).

The decline of the differentiation capacity in the control cultures was not accompanied by changes in proliferation rates of myoblasts. No evidence was found that the proliferation rate was affected by LDR exposure. Without being bound by theory, the inventors believe this may further suggest that the improvement of the differentiation capacity may have been due to qualitative changes in long-term cultures enabling enhanced retention of muscle identity.

The observed effect may have implications in stem cell-based therapies of muscle disease. One current limitation of such therapeutic approaches is the necessity to expand muscle stem cells, either in ex vivo cultures of patient-derived muscle stem cells or in in vitro cultures of muscle stem cells produced by directed differentiation from hES or ihPS cells. Preconditioning of cells in such cultures using LDR may help reinforce retention of their myogenic functional properties otherwise negatively affected by long-term culture conditions. This may help improve overall therapeutic efficacy. It has been shown that LDR improves retention of muscle-specific identity in C2C12 mouse myoblasts subjected to multiple rounds of growth→differentiation→reserve cell isolation. Such improvement may find wide use in regenerative medicine, specifically in prospective stem cell-based therapies of various muscle diseases.

Example 2

In accordance with another broad aspect of the teaching described herein, the effects of LDR on mesenchymal and endothelial stem cells were investigated in accordance with the methods described herein.

Materials and Methods
Cell Culture

In this example, umbilical cord blood (UCB) derived mesenchymal stromal/stem and progenitor cells (MSPCs) were obtained from American Type Culture Collection (ATCC, Manassas, Va., USA) and expanded in UCB mesenchymal stem cell (MSC) expansion medium (# PCS-500-030 and PCS-500-040, ATCC) following manufacturer's instructions. Endothelial colony forming cells (ECFCs) were derived from fresh cord blood units (Canadian Blood Services, Ottawa, ON, CA) according to an approved ethical protocol (Veritas Independent Research Board). Cord blood was processed using Ficoll Paque Plus density separation gradient (GE Healthcare Bio-Sciences AB, Uppsala, Sweden) to yield mononuclear cells (MNCs). MNCs were plated in CellBind coated 6-well plates (#3335, Corning, N.Y., USA) and supplemented with ECFC expansion medium (# CC-3162, Lonza Group Ltd., Basel, Switzerland). Medium was changed every 2-3 days. All cells were allowed to adhere and expand in a standard humidified $CO_2$ incubator at 37° C.

Once 80% confluency was reached for MSPC cultures and visible dense endothelial colonies emerged in ECFC cultures cells were passaged—p1. Individual ECFC colonies/clones were passaged separately using DOW Corning high vacuum Grease (DOW Corning Corporation, Midland, Mich., USA) coated glass rings and seeded into separate wells in a 6-well plate at $2.5 \times 10^3$ cells/cm2 and further expanded to p2 and in p100 to p3-4. Passaged MSPCs were re-plated into p100 plates at $3.0 \times 10^3$ cells/cm2 and expanded to p2-4. At p4 all cells were acutely irradiated with 0, 10, 50 and 100 mGy gamma rays using Gamma Cell 200 cell irradiator (Atomic Energy of Ganda Ltd., Chalk River, ON, CA) and allowed to age in culture. ECFC experiments utilized three different clones: 3-2, 3-3 and 13 representing biological replicates. The experiments were performed, at least, in duplicate.

Functional Analyses

Aging was defined in this case as a gradual decline in proliferative capacity (function) of cultured cells. A passage at which cell culture was deemed "aged" differed for MSPCs and ECFC clones and was determined to be p15 for MSPCs, p5 for ECFC clone 3-2, p8 for ECFC clone 13 and p11 for ECFC clone 3-3. Growth curves for cell cultures were constructed based on percent confluency measurements performed by Incucyte instrument (Essen Bioscience, Inc., Ann Arbor, Mich., USA). Incucyte was used to take images of cells with 4× and 10× objective every hour of cell culture at every passage. Cell proliferation was measured as doubling time in the linear portion of the cell growth curve, usually between 20-80% confluency. The following formula was used for doubling time calculations:

$$(t2-t1)/(3.32 \times (\log n2 - \log n1)), \text{ where}$$

t2—final time point
t1—initial time point
n1—number of cells/confluency at t1
n2—number of cell/confluency at t2

Migration of ECFC cells was measured using scratch-wound assay and a Cell Migration Kit (#4493, Essen Bioscience) according to manufacturer's instructions. Briefly, cells were seeded in a specialized 96-well plate at 90-100% confluency and allowed to adhere. All wells in the plate were scratched using a specially designed wound maker that allows for consistent scratched to be performed to minimize well-well variation. A plate was placed in Incucyte instrument and monitored for 24 hrs, every hour an image was obtained using a 10× objective. The migration analysis was based on two measurements: 1) amount of time it took to "heal" the wound to 60% confluency; and 2) the confluency of the wound at 10 hrs post scratch. All values were expressed relative to p4 non-irradiated cells. This assay was performed with 5 replicates, on 2 clones: 3-2 and 3-3 with aged cells representing p6 and p13, respectively.

Aged MSPCs were differentiated along chondrogenic lineage for 14 days using human MSC differentiation kit (# SC006, R&D System Inc., Minneapolis, Minn., USA) following manufacturer's instructions. Briefly, p5 and 15 cells were spun down to create a pellet and differentiated, with fresh medium changes performed every 2-3 days. Chondrocytic pellets were sectioned at 10 um using a cryostat (CM 3050, Leica Biosystems Inc., Concord, ON, CA) and fluorescently stained with anti-aggrecan antibody. Aggrecan is a protein that is specifically produced in chondrocytes and act as a marker of chondrocytic differentiation. Images of pellet sections were captured with a 10× objective using Evos FL fluorescent microscope (Thermo Fisher Scientific, Waltham, Mass., USA). Fluorescent staining was quantitated using ImageJ software (ImageJ v. 1.52b, National Institutes of Health, USA; http://imagej.nih.gov/ij) that measures Raw Integrated Intensity of all pixels in the image. All values were normalized to p5 untreated control and experiments were performed in duplicate.

Statistical Analysis

All values were plotted relative to untreated (UT) early passage (p4 or p5) cells. Treated aged groups were compared to untreated aged control at the same passage and significance was determined using a paired, one-tailed student's t-test with p<0.5 representing significant changes.

Results and Discussion

Delayed Aging of Low-Dose Irradiated Cells

Figure 8:
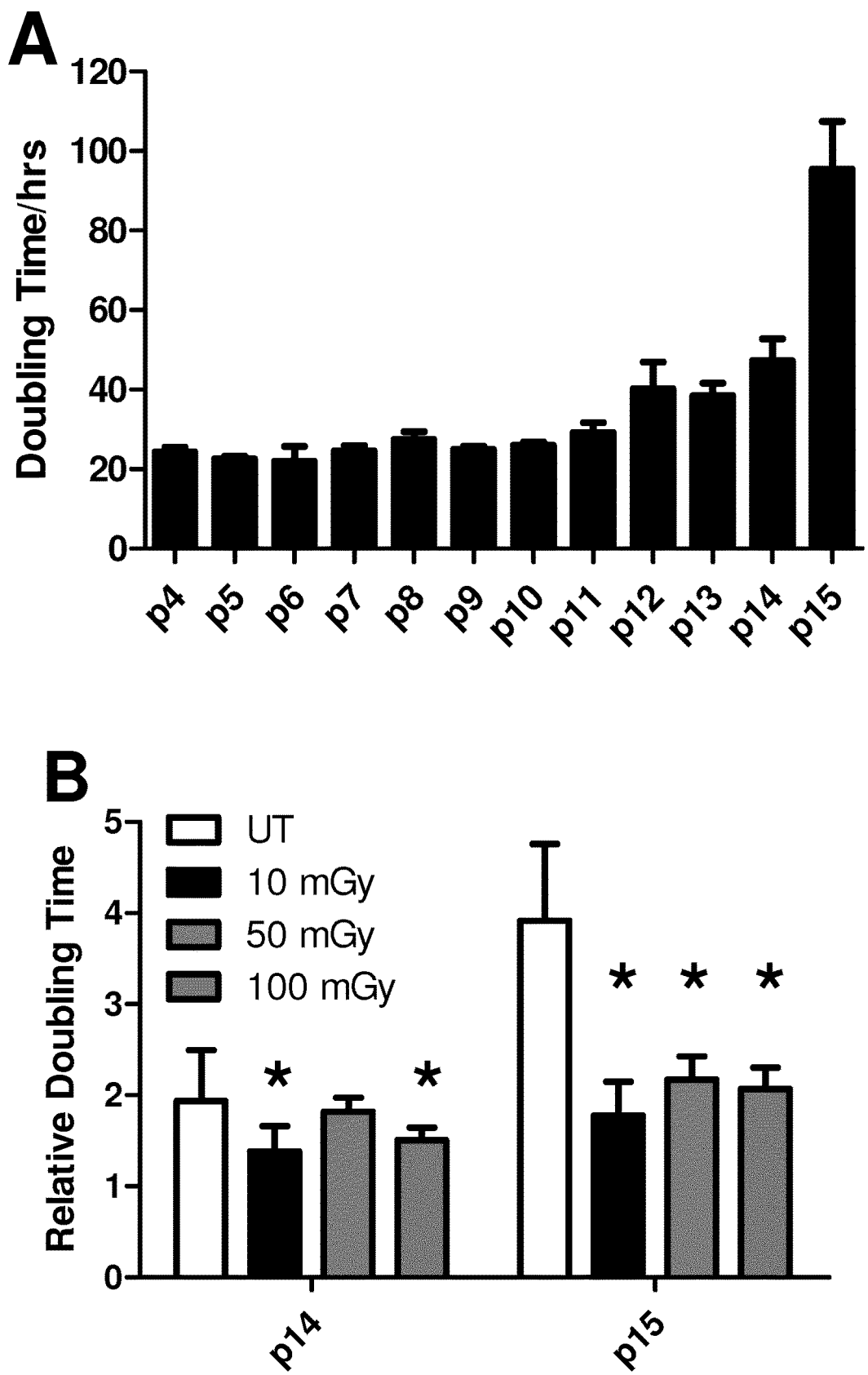
FIG. 8 shows delayed aging in irradiated MSPC cultures. A: Doubling time increased from 24.4 to 95.5 hrs for MSPCs as they aged in culture from p4 to p15. B: p4 cell were irradiated at 10, 50 and 100 mGy and allowed to age to p14 and p15. Measurements of doubling time were performed and plotted relative to doubling time of p4 untreated controls. Irradiated groups were compared to untreated control at the same passage. *Asterisks denote significant changes, $p<0.5$.
Figure 9:
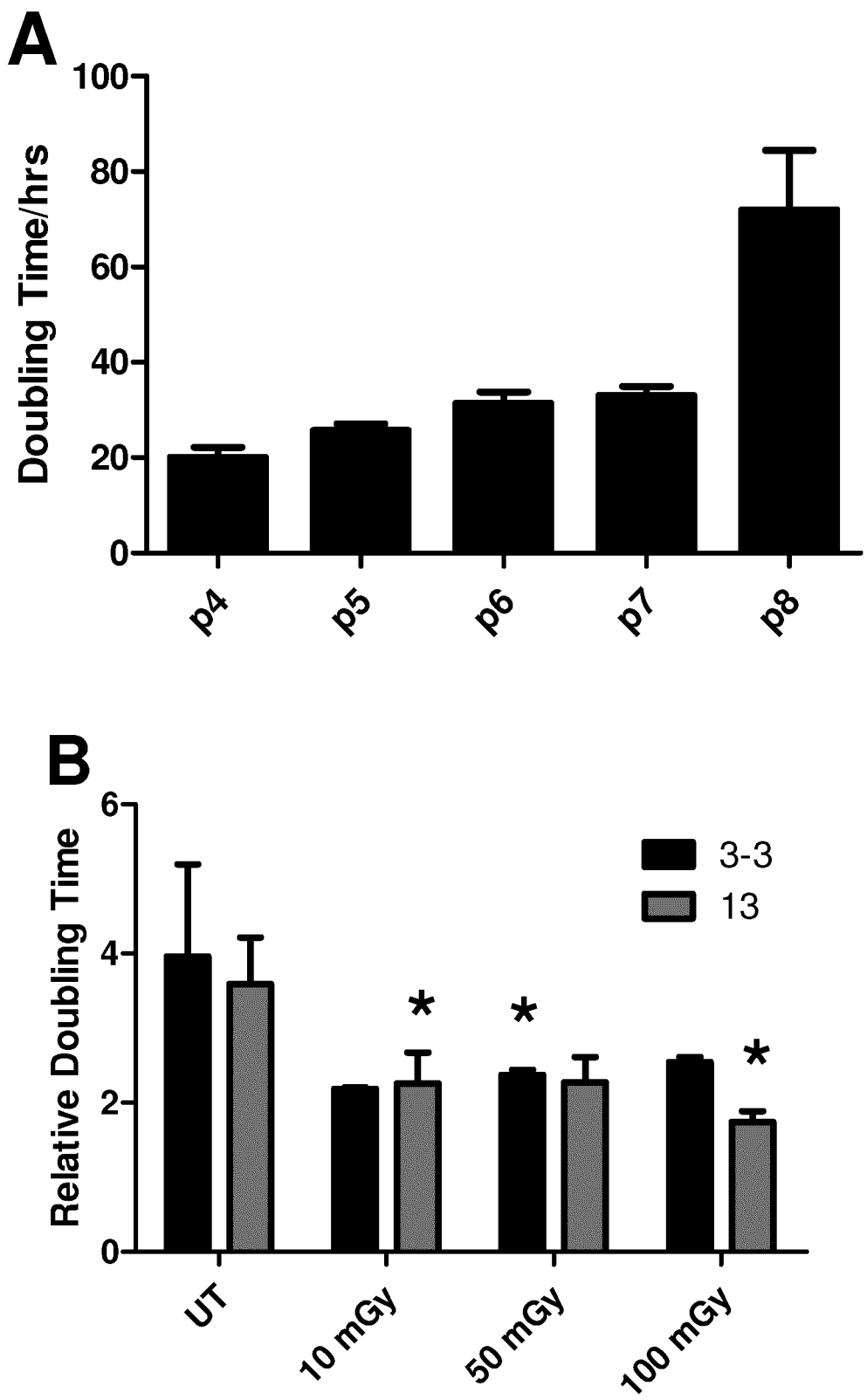
FIG. 9 shows delayed aging in irradiated ECFC cultures. A: Doubling time increased from 20.0 to 71.9 hrs for ECFC clone 13 as the cells aged in culture from p4 to p8. B: p4 cells were irradiated at 10, 50 and 100 mGy and allowed to age to p8. Measurements of doubling time were performed and plotted relative to doubling time of p4 untreated controls. Irradiated groups were compared to untreated control at the same passage. *Asterisks denote relatively significant changes, $p<0.5$.

To test the effects of LDR on aging of stem cells in culture, images of untreated and irradiated cell cultures were captured every hour for every passage and percent confluency of the cell monolayer was measured. Using these values a growth curve was constructed and the doubling time of cells was determined as described in Materials and Methods. FIG. 8A depicts changes in doubling time of MSCPs as they age from p4 to p15 with a relatively significant decrease in proliferation noted at p14-15. Similar observations were made for ECFCs with FIG. 9A representing the aging process of ECFC clone 13. Interestingly, when MSPCs and ECFCs are irradiated at early passage and allowed to age in culture, the aging process is delayed. FIGS. 8B and 9B demonstrate the delay in aging for MSPCs and ECFCS, respectively, as measured by decreased doubling time for irradiated groups vs. untreated controls.

Figure 10:
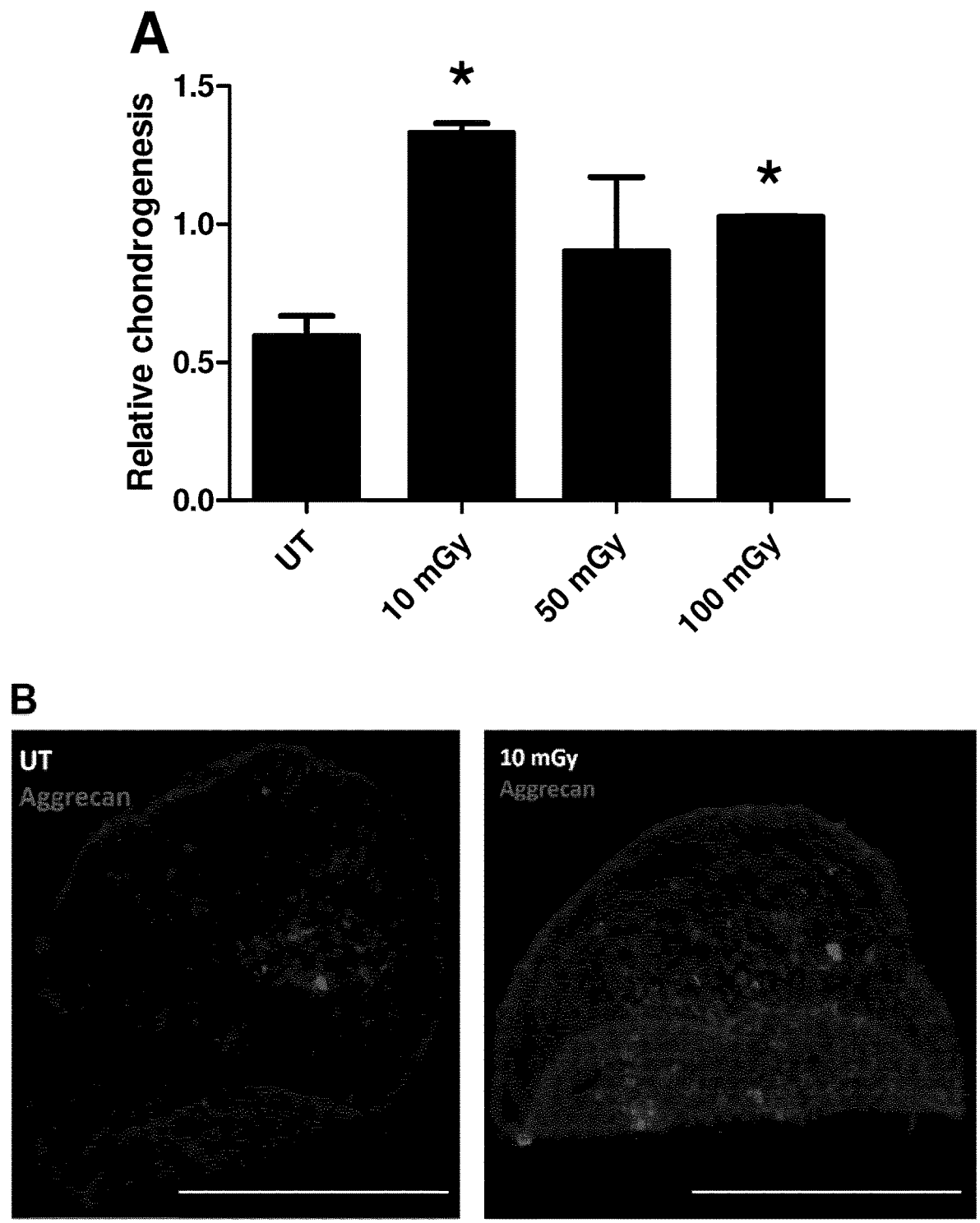
FIG. 10 shows increased chondrogenic differentiation of irradiated aged MSPCs. Young, p4 cells were acutely irradiated at 10, 50 and 100 mGy gamma rays and allowed to age to passages 5 and 15. p5 and p15 irradiated cells were then differentiated along chondrogenic lineage for 14 days in chondrogenic differentiation medium. Resultant chondrocytic pellets were processed, sectioned and stained for aggrecanas described in Materials and Methods. A: Total fluorescent intensity of the pellet sections was quantified using ImageJ's Raw Integrated Density calculations. All values were normalized to untreated p5 controls. *Asterisks denote statistically significant (p<0.05) changes. B: Representative stained chondrocyte sections derived from aged p15 untreated (UT) and 10 mGy irradiated cell pellets. Experiments were performed in duplicate. White bar represents 400 um.

Increased Functional Capacity of MSPCs as Measured by Increased Chondrogenic Differentiation One of the defining features of mesenchymal stem/stromal cells is their ability to differentiate into cells of skeletal lineages such as chondrocytes. To test the effects of LDR on changes in functional capacity of MSPCs, passage 5 and 15 cells previously irradiated at p4 were differentiated along chondrogenic lineage. Following 14 days of differentiation chondrocyte pellets were sectioned and stained for aggrecan, amount of staining was quantified and is depicted in FIG. 10A. Differentiation capacity of p15 cells was expressed relative to differentiation of young p5 MSPCs. There was an approximate 2× decrease in chondorgenic differentiation in untreated aged cells vs. untreated young controls. However, upon LDR treatment aged cells maintained and even improved their differentiation potential, e.g., 10 mGy condition. The representative images of chondrocyte pellet sections for aged UT and aged 10 mGy groups are shown in FIG. 10B.

Figure 11:
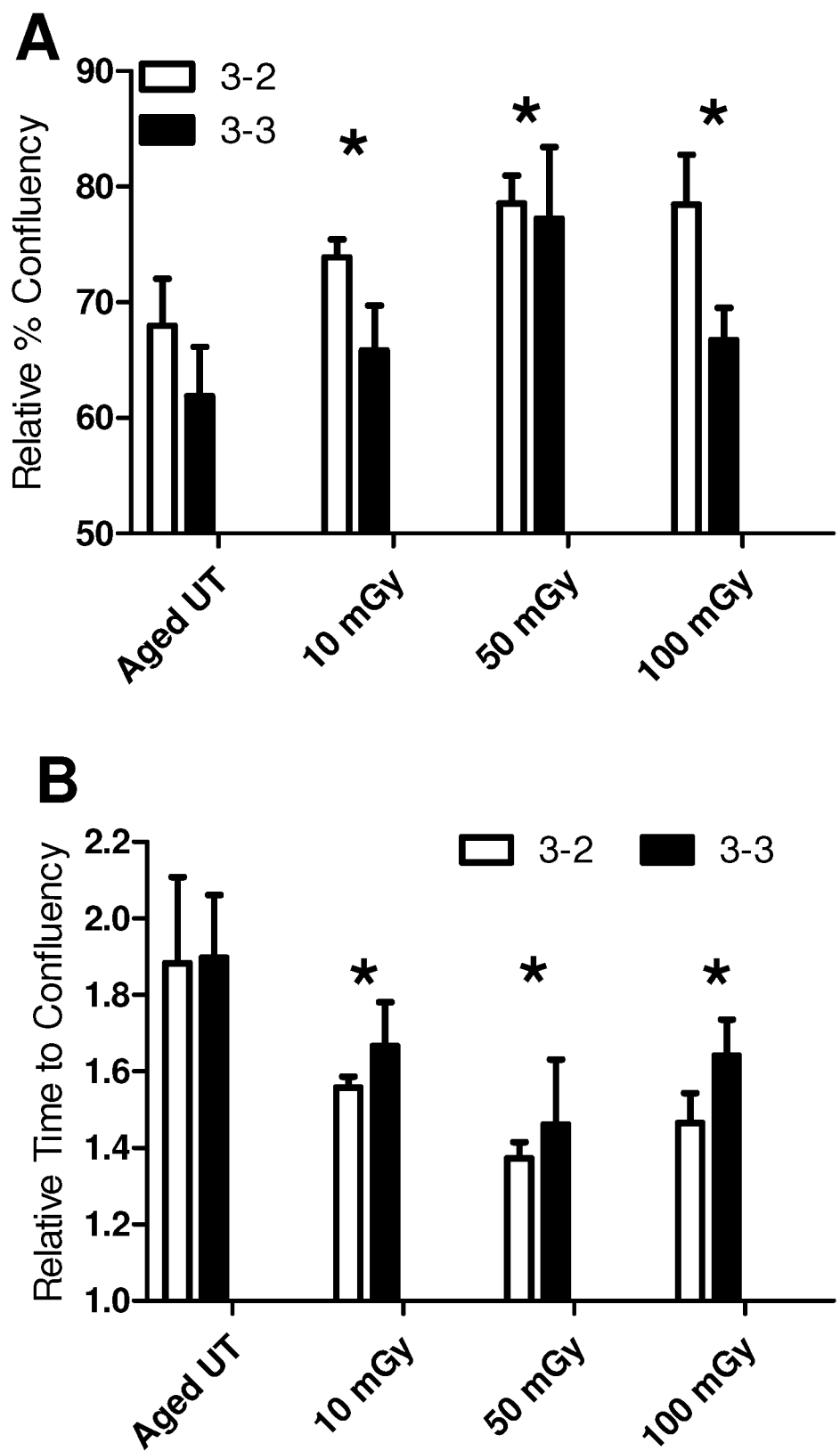
FIG. 11 shows increased migration of irradiated aged ECFCs. Data represents a scratch wound assay. A wound was created in the cell monolayer. Cells were monitored for 24 hrs and their migration capacity was estimated by the speed of wound closure. A: Confluency of the wound was measured at 10 hrs post scratch for aged untreated and treated cells and expressed relative to the confluency achieved by young (p4) untreated cells. B: The time to achieve 60% confluency was estimated for aged untreated and treated cells and expressed relative to the confluency achieved by young (p4) untreated cells. *Asterisks denote significant changes, p<0.5.

Increased Functional Capacity of Low-Dose Irradiated ECFC Cells as Measured by Enhanced Migration:

To evaluate the effects of LDR on the functional capacity of ECFCs, cell migration assays were performed. One of the most important functional attributes of endothelial stem cells is their ability to travel/migrate to the site of tissue damage and repair vascular networks. To test ECFC migratory capacity scratch wound assays were performed with untreated and irradiated aged ECFCs. All values were expressed relative to young (i.e. non-aged) untreated (i.e. non-irradiated) controls. Two separate measurements were performed as described in Materials and Methods section. FIG. 11A depicts relative percent confluency of the wound at 10 hrs after the scratch was made and FIG. 11B summarizes the relative time it took for cells to reach 60% confluency within the wound. It is evident from both graphs that aged cells demonstrate decreased migration in comparison to young cells, e.g., they are ~70% as efficient at reaching confluency and taking ~1.8 times longer to close the wound. However, aged irradiated cells while not performing as well as the young cells still maintain majority of their migratory capability. FIG. 11 thus demonstrates a delayed aging capacity of irradiated ECFCs when they are expanded in culture as evident by the significant increase in their migratory capacity in comparison to untreated control.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each individual publication, patent, or patent application was specifically and individually indicated to be incorporated by reference in its entirety.

REFERENCES

1. Sambasivan, R.; Tajbakhsh, S., Skeletal muscle stem cell birth and properties. *Seminars in Cell & Developmental Biology* 2007, 18, 870-882.
2. Charge, S. B. P.; Rudnicki, M. A., Cellular and Molecular Regulation of Muscle Regeneration. *Physiological Reviews* 2004, 84, 209-238.
3. Aziz, A.; Sebastian, S.; Dilworth, F. J., The Origin and Fate of Muscle Satellite Cells. *Stem Cell Reviews and Reports* 2012, 8, 609-622.
4. Bengal, E.; Perdiguero, E.; Serrano, A.; Muñoz-Cánoves, P., *Rejuvenating stem cells to restore muscle regeneration in aging* [version 1; referees: 3 approved]. 2017; Vol. 6.
5. Grist, C., Emerging new tools to study and treat muscle pathologies: genetics and molecular mechanisms underlying skeletal muscle development, regeneration, and disease. *The Journal of Pathology* 2017, 241, 264-272.
6. Kuang, S.; Rudnicki, M. A., The emerging biology of satellite cells and their therapeutic potential. *Trends in Molecular Medicine* 2008, 14, 82-91.
7. Tedesco, F. S.; Dellavalle, A.; Diaz-Manera, J.; Messina, G.; Cossu, G., Repairing skeletal muscle: regenerative potential of skeletal muscle stem cells. *The Journal of Clinical Investigation* 2010, 120, 11-19.
8. Maffioletti, S. M.; Gerli, M. F. M.; Ragazzi, M.; Dastidar, S.; Benedetti, S.; Loperfido, M.; VandenDriessche, T.; Chuah, M. K.; Tedesco, F. S., Efficient derivation and inducible differentiation of expandable skeletal myogenic cells from human ES and patient-specific iPS cells. *Nat. Protocols* 2015, 10, 941-958.
9. Chal, J.; Oginuma, M.; Al Tanoury, Z.; Gobert, B.; Sumara, O.; Hick, A.; Bousson, F.; Zidouni, Y.; Mursch, C.; Moncuquet, P.; Tassy, O.; Vincent, S.; Miyanari, A.; Bera, A.; Garnier, J.-M.; Guevara, G.; Hestin, M.; Kennedy, L.; Hayashi, S.; Drayton, B.; Cherrier, T.; Gayraud-Morel, B.; Gussoni, E.; Relaix, F.; Tajbakhsh, S.; Pourquie, O., Differentiation of pluripotent stem cells to muscle fiber to model Duchenne muscular dystrophy. *Nat Biotech* 2015, 33, 962-969.
10. Calabrese, E. J., Preconditioning is hormesis part I: Documentation, dose-response features and mechanistic foundations. *Pharmacological Research* 2016, 110, 242-264.
11. Calabrese, E. J., Pre- and post-conditioning hormesis in elderly mice, rats, and humans: its loss and restoration. *Biogerontology* 2016, 17, 681-702.
12. Baldwin, J.; Grantham, V., Radiation Hormesis: Historical and Current Perspectives. *J Nucl Med Technol* 2015, 43, 242-246.
13. Jolly, D.; Meyer, J., A brief review of radiation hormesis. *Australas Phys Eng Sci Med* 2009, 32, 180-187.
14. Mitchel, R. E.; Jackson, J. S.; Morrison, D. P.; Carlisle, S. M., Low doses of radiation increase the latency of spontaneous lymphomas and spinal osteosarcomas in cancer-prone, radiation-sensitive Trp53 heterozygous mice. *Radiat Res* 2003, 159, 320-327.
15. Mitchel, R. E.; Jackson, J. S.; McCann, R. A.; Boreham, D. R., The adaptive response modifies latency for radiation-induced myeloid leukemia in CBA/H mice. *Radiation Research* 1999, 152, 273-279.
16. Osipov, A. N.; Buleeva, G.; Arkhangelskaya, E.; Klokov, D., In vivo γ-irradiation low dose threshold for suppression of DNA double strand breaks below the spontaneous level in mouse blood and spleen cells. *Mutation Research/Genetic Toxicology and Environmental Mutagenesis* 2013, 756, 141-145.
17. Manda, K.; Kavanagh, J. N.; Buttler, D.; Prise, K. M.; Hildebrandt, G., Low dose effects of ionizing radiation on normal tissue stem cells. *Mutation Research/Reviews in Mutation Research* 2014, 761, 6-14.
18. Alessio, N.; Del Gaudio, S.; Capasso, S.; Di Bernardo, G.; Cappabianca, S.; Cipollaro, M.; Peluso, G.; Galderisi, U., Low dose radiation induced senescence of human mesenchymal stromal cells and impaired the autophagy process. *Oncotarget* 2015, 6, 8155-8166.
19. Masuda, S.; Hisamatsu, T.; Seko, D.; Urata, Y.; Goto, S.; Li, T. S.; Ono, Y., Time- and dose-dependent effects of total-body ionizing radiation on muscle stem cells. *Physiological Reports* 2015, 3, e12377-e12377.
20. Yang, L.; Liu, Z.; Chen, C.; Cong, X.; Li, Z.; Zhao, S.; Ren, M., Low-dose radiation modulates human mesenchymal stem cell proliferation through regulating CDK and Rb. *Am J Transl Res* 2017, 9, 1914-1921.
21. Sousa-Victor, P.; Muñoz-Cánoves, P., Regenerative decline of stem cells in sarcopenia. Molecular Aspects of Medicine 2016, 50, 109-117.
22. Yaffe, D.; Saxel, O. R. A., Serial passaging and differentiation of myogenic cells isolated from dystrophic mouse muscle. *Nature* 1977, 270, 725-727.
23. Azzam, E. I.; Raaphorst, G. P.; Mitchel, R. E. J., Radiation-Induced Adaptive Response for Protection against Micronucleus Formation and Neoplastic Transformation in C3H 10T1/2 Mouse Embryo Cells. *Radiation Research* 1994, 138, S28-S31.
24. Ng, R. K.; Gurdon, J. B., Epigenetic memory of an active gene state depends on histone H3.3 incorporation into chromatin in the absence of transcription. *Nat Cell Biol* 2008, 10, 102-109.
25. Miousse, I. R.; Kutanzi, K. R.; Koturbash, I., Effects of ionizing radiation on DNA methylation: from experimental biology to clinical applications. *Int J Radiat Biol* 2017, 93, 457-469.
26. Chiche, A.; Le Roux, I.; von Joest, M.; Sakai, H.; Aguín, S. B.; Cazin, C.; Salam, R.; Fiette, L.; Alegria, O.; Flamant, P.; Tajbakhsh, S.; Li, H., Injury-Induced Senescence Enables In Vivo Reprogramming in Skeletal Muscle. *Cell Stem Cell* 2017, 20, 407-414.e404.

The invention claimed is:

1. A method of preconditioning muscle stem cells, the method comprising:
   a) providing a sample comprising a plurality of target muscle stem cells;
   b) irradiating the target muscle stem cells with a low dose of radiation comprising between 10 and 100 mGy of radiation emitted from a radiation source during an irradiation period to convert the target muscle stem cells to irradiated, preconditioned muscle stem cells suitable for use in a subsequent therapeutic treatment process;
   wherein irradiating the target muscle stem cells reduces age-associated decline of at least a first cellular function of each target muscle stem cell.

2. The method of claim 1, wherein the first cellular function is cellular fusion, the initial performance value comprises an initial fusion index, the aged performance value comprises an aged fusion index, and the treated performance value comprises a treated fusion index, wherein the treated fusion index is greater than the aged fusion index.

3. The method of claim 2, wherein the treated fusion index is at least twice the aged fusion index.

4. The method of claim 2, wherein the preconditioned muscle stem cells show increased differentiation into muscle fibers compared to target muscle stem cells that are not irradiated.

5. The method of claim 2, wherein the preconditioned muscle stem cells have higher expression of at least one marker selected from the group consisting of myogenin, MyH3, MyoD, TKS5 and TMEM8c compared to target muscle stem cells that are not irradiated.

6. The method of claim 1, wherein the radiation comprises low linear energy transfer (LET) ionizing radiation and comprises γ-radiation.

7. The method of claim 1, wherein dose of radiation is 10 mGy.

8. The method of claim 1, further comprising administering the preconditioned muscle stem cells to a subject in need thereof, wherein the subject is a human and wherein the subject has a muscle disease.

9. A method of treating a muscle disease comprising administering preconditioned stem cells is obtained by using the method of claim 1 to a subject in need thereof.

10. The method of claim 1, wherein the first cellular function having an initial performance value and defining an aged performance value at a threshold aging time, and wherein the preconditioned stem cells have a treated performance value at the threshold aging time that is between the aged performance value and the initial performance value.

11. The method of claim 1, wherein the treated fusion index is more than 60%.

12. The method of claim 1, wherein first dose of radiation is 50 mGy.

13. The method of claim 1, wherein first dose of radiation is 100 mGy.

* * * * *